(12) United States Patent
Goodman et al.

(10) Patent No.: US 6,268,339 B1
(45) Date of Patent: Jul. 31, 2001

(54) LANTHIONINE BRIDGED PEPTIDES

(75) Inventors: Murray Goodman; George Osapay, both of La Jolla, CA (US)

(73) Assignee: Winfried Kolbeck, Munich (DE)

( * ) Notice: Subject to any disclaimer, the term of this patent is extended or adjusted under 35 U.S.C. 154(b) by 0 days.

(21) Appl. No.: 09/384,061

(22) Filed: Aug. 26, 1999

Related U.S. Application Data

(63) Continuation of application No. 08/467,472, filed on Jun. 6, 1995, now Pat. No. 6,028,168, which is a continuation-in-part of application No. 08/021,606, filed on Jan. 28, 1993, now abandoned, which is a continuation of application No. 07/742,908, filed on Aug. 9, 1991, now abandoned.

(51) Int. Cl.[7] .............................. A61K 38/12; C07K 5/12
(52) U.S. Cl. ................. 514/11; 514/14; 514/15; 514/16; 514/17; 530/302; 530/307; 530/315; 530/317; 930/50
(58) Field of Search .................... 530/302, 307, 530/315, 317; 514/14–17, 11; 930/50

(56) References Cited

U.S. PATENT DOCUMENTS

| | | | |
|---|---|---|---|
| 3,446,789 | 5/1969 | Rudinger et al. | 260/112.5 |
| 3,980,631 | 9/1976 | Procházka et al. | 260/112.5 |
| 4,148,786 | 4/1979 | Sarantakis | 260/112.5 |
| 4,161,521 | 7/1979 | Veber et al. | 424/177 |
| 4,322,339 | 3/1982 | Gesellchen et al. | 260/112.5 |
| 4,349,544 | 9/1982 | Cort et al. | 424/177 |
| 4,482,486 | 11/1984 | Brtnik et al. | 260/112.5 |
| 4,483,794 | 11/1984 | Barth et al. | 260/112.5 |
| 4,518,711 | 5/1985 | Hruby et al. | 514/11 |
| 6,028,168 * | 2/2000 | Goodman et al. | 530/317 |

FOREIGN PATENT DOCUMENTS

93/03056 * 2/1993 (WO).

OTHER PUBLICATIONS

CA: 125:317643q of Lee et al., Pept. 1994 Proc. Eur. Pept. Symp. 23rd 1994 pp. 627–628, 1995.*

CAPLUS AN:1978:417351 to Ling et al., Pept. Proc. Am. Pept. Symp. 5th 96–9, 1995.*

Harpp and Gleason, "Preparation of Mass and Spectral Properties of Cystine and Lathinone Derivatives. A Novel Synthesis at L–Lanthinone by Selective Desulfurization", Department of Chemistry, McGill University, Montreal, Canada, *J. Org. Chem*, vol. 36, No. 1, 1971 pp. 73–80.

Hruby, "Minireview, Conformational Restrictions of Biologically Active Peptides via Amino Acid Side Chain Groups".

Degrado, "Design of Peptides and Proteins" excerpt from "Advances in Protein Chemistry", vol. 39, pp. 51–67.

Olsen et al. "Conversion of Thiosulfate Derivatives of Cystine to Unsymmetrical Cystines and Lanthionones by Reaction with Tris (dialky/amino) phosphines" Department of Chemistry and Biochemistry, Utah State University, *J. Org. Chem.*, 1985, 50, 4332–4336.

Bean, et al., "Identification of a thioether by–product in the synthesis of a cyclic disulfide peptide by tandem mass spectrometry" printed at pp. 443–445 of "Peptides: Chemistry, Structure and Biology".

Proceedings of the Twenty–Third European Peptide Symposium, "Peptides 1994", Editor: Hernani L.S.Maia.

* cited by examiner

*Primary Examiner*—Bennett Celsa
(74) *Attorney, Agent, or Firm*—Norris McLaughlin & Marcus

(57) ABSTRACT

Disclosed are lanthionine bridged peptides having the structure

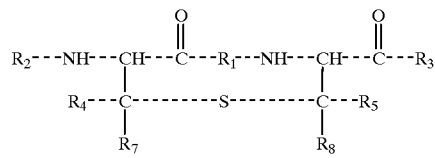

methods of their preparation and their use as pharmacologically active agents.

12 Claims, 4 Drawing Sheets

LANTHIONINE BRIDGED PEPTIDES

This application is a Continuation of Ser. No. 08/467,472 filed Jun. 6, 1995 now U.S. Pat. No. 6,028,168 which in turn was a Continuation-in-Part of Ser. No. 08/021,606 filed Jan. 28, 1993, now abandoned, which in turn was a Continuation of Ser. No. 07/742,908 filed Aug. 9, 1991, now abandoned.

It is a basic goal in peptide chemistry to design molecules for medical or industrial application. Design means that naturally occurring peptides which have a biological activity are modified in order to obtain molecules which have advantages over the naturally occurring peptides in different respects. There are several groups of peptides which act as hormones, as neurotoxins or as plant regulating agents. These peptides are usually small, flexible molecules which may optionally have a disulfide bridge.

SUMMARY OF THE INVENTION

It is an object of the present invention to provide peptides which comprise a monosulfide bridge. This thioether bond is also designated as a lanthionine bridge and corresponds with the cystine bridge with the exception that the disulfide bridge is replaced by a monosulfide linkage. Two amino acid residues having the general formula

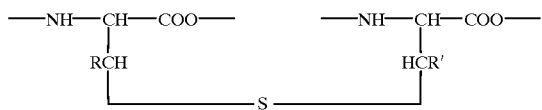

are designated to be joined into a lanthionine bridge wherein the linkage of the two amino acids has the meaning —RCH—S—HCR'—, wherein R and R' respectively represent —H, a lower ($C_1$–$C_{10}$) alkyl or aralkyl group. In a preferred embodiment R and R' are H. The amino acid termini of the lanthionine structure are designated as $Ala_L$ if R and R' are H and $Thr_L$ when R or R' are $CH_3$. Other β-substituted lanthionine components are designated as substituted $Ala_L$ derivatives, e.g. βethyl$Ala_L$.

DESCRIPTION OF THE RELATED ART

Thioether bonus of the lanthionine type are known from some fungal toxins and antibiotics, for example from the lantibiotics, as nisin, epidermin, dunamycin or mersacidin. Naturally occurring compounds having the monosulfide bridge always have more than two monosulfide bridges in the molecule.

M. F. Bean et al. have reported in their article "Identification of a Thioether By-product in the Synthesis of a Cyclic Disulfide Peptide by Tandem Mass Spectrometry" as published in the Proceedings of the 11th American Peptide Symposium, ESCOM, (Leiden 1990, p. 443) on a somatostatin analog wherein the internal disulfide bond has been converted to a thioether link. The somatostatin analog with the putative amino acid sequence D-Phe-$Ala_L$-Phe-Trp-Lys-Thr-$Ala_L$-Thr(ol), wherein the two $Ala_L$ residues are linked via the thioether bridge, has been described as the by-product which was obtained by the Boc-TFA-preparation of sandostatin analogs. The originally occurring somatostatin derivative has a disulfide bridge.

BRIEF DESCRIPTION OF THE DRAWINGS

The invention will now be described in greater detail with reference to the drawings, wherein.

DETAILED DESCRIPTION OF THE INVENTION

Figure 1:
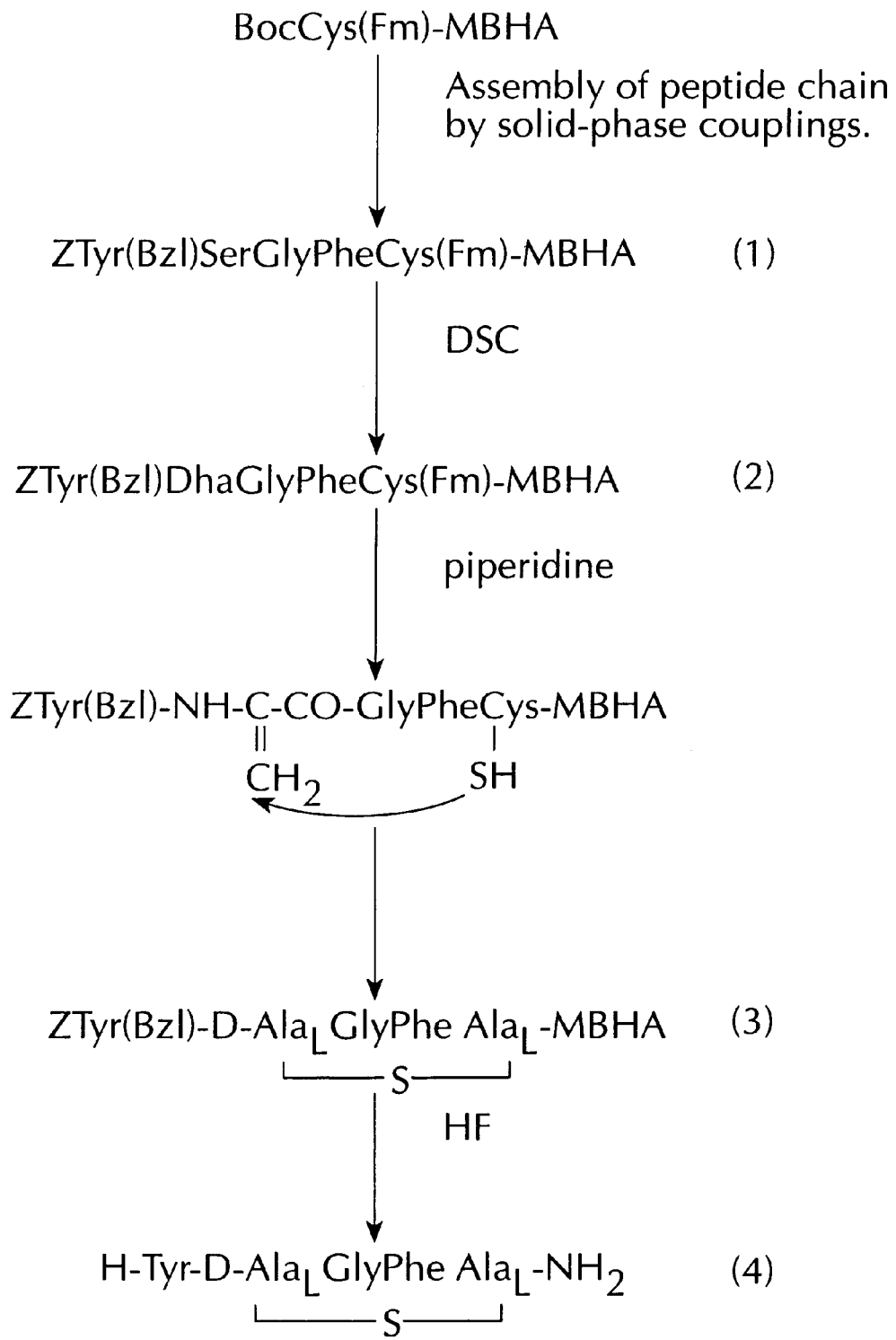
FIGS. 1–4 describe different syntheses of lanthionine bridged compounds.

It is an object of the present invention to provide analogs or fragments thereof of peptide compounds having at least one monosulfide bridge in the molecule and exhibiting an improved biological activity. The analogs of peptide compounds according to the invention comprise analogs of compounds, such as: virus related peptides, such as peptides of HIV, fragments of oncogenes, atrial natriuric peptides, epidermal growth factors, transforming growth factor and fragments thereof, spanolysin, TRP, xenopsin, PGL, PGA, custracean, bactenecin, relaxin, cyclotheonamides, casoxin D, mastoparan, azaline-B, GRF (growth hormone releasing factor), leucinostatins, didemnins, nazumamides, theonellamides, glicentin, aureobasidins, guanylin, NGF (nerve growth factor), gluten exorphins, pardaxin P-1, neuromedin U (NMU), bactenecins, bacitracin, bombyxin, PTH, PTHrP (parathyroid hormon-related protein), agelenin, insulin, glucagon, tyrocidins, polymyxins, valinomycin, conotoxins and related neurotoxins, mast cell degranulating peptides (MCD), HIV gp41 antigenic peptide 1 or peptide 4, TNF (tumor necrosis factor), RGD-peptides (peptides containing the sequence . . . -Arg-Gly-Asp- . . . ).

It is an especially preferred embodiment of the present invention to provide analogs of peptides which are acyclic such as: ACTH-analogs, angiotensins, magainin, magainin peptides (PGS), bombesin, bradykinin, fragments of fibronectin, LHRH-analogs, neuropeptides, neurokinins, neurotensins, thymosine, fragments of thymopoeitin, caerulein, dermorphin, sauvigine, tachikinin, MSH (melanocyte stimulating hormone), cecropins, palindromic peptides, beta-thymosins, GIF (growth inhibitory factor), hirudin and fragments thereof, VIC (vasoactive intestinal contractor), cholecystokinins (CCK), amyloids, substance P, gastrin, melittin, secretin, gramicidin A and gramicidin S, urotensin I and II, In an especially preferred embodiment of the present invention the peptide or the fragment thereof having the thioether bond is derived from a molecule having the biological activity which is in the naturally occurring form linear.

In a preferred embodiment of the present invention the peptide has not more than two monosulfide bridges and in an especially preferred embodiment the peptide has only one monosulfide bridge.

In a further preferred embodiment of the present invention the naturally occurring molecule has two or more cyclic structures wherein at least one cycle is formed by a thioether bond.

The compounds of the present invention have a higher biological activity than the corresponding naturally occurring peptides.

According to the present invention lanthionine-bridged peptides are disclosed having the general formula

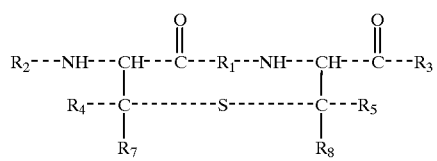

wherein $R_1$ is selected from the group consisting of sequences of 2 to 7 amino acids selected from naturally occurring amino acids and the D-enantiomers thereof and peptidomimetrics;

$R_2$ is selected from the group consisting of
a] —H, $C_{1-8}$ alkyl, $C_{7-12}$ aralkyl, —HCO, $C_{2-18}$ acyl or $C_{2-18}$ aracyl,
b] a naturally occurring amino acid or sequence of up to 25 amino acids where the —N terminal —$NH_2$ group is present or is replaced by $C_{1-8}$ alkyl, $C_{7-12}$ aralkyl, —HCO, or $C_{2-18}$ acyl, —OH, —H or —$NHCOR_6$, and
c] peptidomimetics;

$R_3$ is selected from the group consisting of
a] —OH, $NH_2$;
b] naturally occurring amino acids or sequences of up to 25 amino acids where the —C terminal —COOH is present or is replaced by —$CONH_2$ or —$CH_2OH$;
c] peptidomimetics; and

may be replaced by $CH_2OH$;
with the proviso that $R_1$ is not Phe-Trp-Lys-Thr when $R_2$ is Phe and $R_3$ is Thr[ol];
$R_4$, $R_5$, $R_7$ and $R_8$ are independently hydrogen, cyclohexyl or a substituted or unsubstituted $C_{1-10}$ alkyl; and
$R_6$ is an alkyl or aralkyl residue.

In a preferred embodiment of the present invention $R_4$, $R_5$, $R_7$ and $R_8$ independently represent hydrogen or a methyl group.

The amino acids can be selected from the group consisting of the naturally occurring amino acids including the L-enantiomers and the D-enantiomers. The group of naturally occurring amino acids comprises alanine, arginine, asparagine, aspartic acid, cysteine, cystine, glutamic acid, glutamine, glycine, histidine, hydroxyproline, isoleucine, leucine, lysine, methonine, phenylalanine, proline, serine, threonine, tryptophan, tyrosine, valine, β-analine, χ-aminobutyric acid, betaine, carnitine, citrulline, creatine, ornithine, saccharopine, 3,4-dihydroxyphenylalanine, 5-hydroxytryptophan, thyroxine, homocysteine, S-methylmethionine, penicillamine, pipecolic acid and nalidixic acid.

A regular peptide has the following structure:

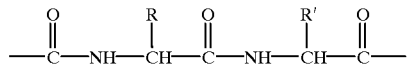

whereas the retro-inverso-structure has the following formula:

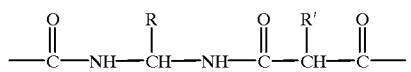

The radicals $R_1$, $R_2$ or $R_3$, can comprise peptidomemetics. Non-natural amino acids which can be used in our invention are identified by the following:
α-methylated amino acids
β-mono and dimethylated amino acids
Tic [7-hydroxy-1,2,3,4-tetrahydroisoquinoline-3-carboxylic acid[
Atc [2-aminotetralin-2-carboxylic acid[
Aic [2-amino-5-hydroxyimolinane-carboxylic acid[
Hat [2-amino-6-hydroxytetralin-2-carboxylic acid[
Nal 2-(1-napththyl)alanine
ΔPhe dehydro-phenylalanine
p-x-Phe p-halogeno-phenylalanine
$Me_3Phe$ 2,-dimethyl-β-methyl-phenylalanine Examples of dipeptide isosteres which may be utilized are:

Benzodiazepine ring:

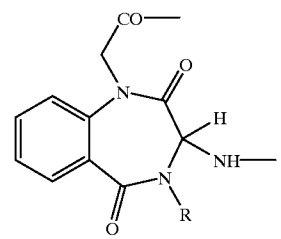

Hydantoin rings:

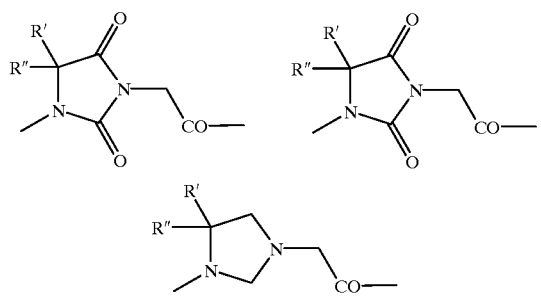

Tetrazole ring:

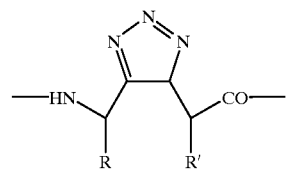

3-oxoimidoliazidine:

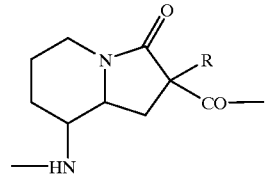

The retro-inverso structure is only one possible modification to the regular peptide structure. The regular structure may be modified by the presence of a thioester structure according to the following formulae:

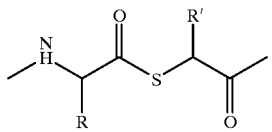

-continued

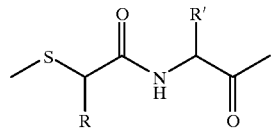

In other embodiments, the regular peptide structure may be modified in accordance with the formula:

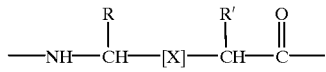

where X is

- CH$_2$—S [methylene thioether]
- CH$_2$—S(O) [methylene sulfoxide]
- CH$_2$—O [methylene ether]
- C(S)—NH [thioamide]
- CO—CH$_2$ [ketomethylene]
- CH$_2$—CH$_2$ [carba]
- NH—NH [aza]
- CH$_2$—NH [methylene amino]

In a preferred embodiment of the present invention the moiety R$_1$ of the peptides according to formula (I) comprises a sequence of from 2 to 4 amino acids.

Preferably the amino acids of the residues R$_2$ and R$_3$ are selected from the group of amino acids comprising D-Phe, D-β-Nal, Tyr, TrpNH$_2$, ThrNH$_2$, Thr(ol). Alternatively the substituents R$_2$ can be H, acyl or aracyl with 1 to 18, preferably 2 to 12 carbon atoms and R$_3$ can have the meaning of —OH or —NH$_2$ and

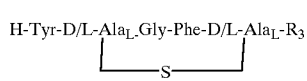

can be replaced by CH$_2$OH. Moreover R$_2$ and R$_3$ respectively can be a short amino acid sequence of Pro-Arg-Gly or Pro-Leu-Gly.

In preferred embodiments of the present invention R$_1$ is represented by a short amino acid sequence selected from the group consisting of Gly-Phe; Phe-D-Trp-Lys-Thr; Phe-D-Trp-Lys-Val; Tyr-Phe-Gln-Asn, Tyr-Ile-Gln-Asn, Tyr-D-Trp-Lys-Val, Gly-Asn-Leu-Ser-Thr, Ser-Asn-Leu-Ser-Thr or Glu-Lys-Asp-Met-Leu-Ser-Ser.

Although the naturally occurring biological active molecules contain mainly the L-enantiomers of the amino acids, in one preferred embodiment of the present invention at least one of the amino acids forming the lanthionine bridge is the D-enantiomer.

Among the especially preferred peptides of the present invention are: lanthionine-enkephalins [SEQ ID NO:1] having the formula (II)

H-Tyr-D/L-Ala$_L$-Gly-Phe-D/L-Ala$_L$-R$_3$
      |_____S_____| wherein R$_3$ is OH or NH$_2$, lanthionine-somatostatins [SEQ ID NO:2 to SEQ ID NO:11] having the general formula (III)

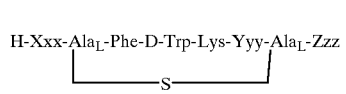

wherein Xxx=D-Phe, D-β-Nal or Phe; Yyy=Thr, Val; Zzz= TrpNH$_2$, ThrNH$_2$ or Thr(ol) with the proviso that Xxx is not Phe when Zzz is Thr(ol) and Yyy is Thr.

Lanthionine-vasopressin [SEQ ID NO:12 and SEQ ID NO:14] having the formula (IV)

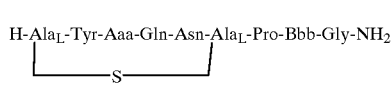

wherein Aaa=Phe and Bbb=Arg, or Leu or Lys lanthionine-oxytocin [SEQ ID NO:13 and SEQ ID NO:15]

(V)

wherein Aaa=Ile and Bbb=Leu or Arg.

Further preferred peptides of the present invention have the formula (VI)

(VI)

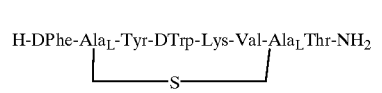

or the formula (VII)

(VII)

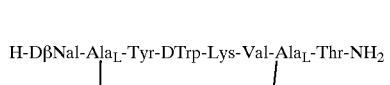

Further preferred peptides [SEQ ID NO:16 to SEQ ID NO:21] have the general formula (VIII)

(VIII)

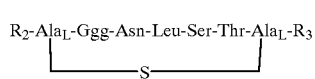

wherein R$_2$ is H, acyl or aracyl, R$_3$ is the fragment 8-32 of human, salmon or eel-calcitonin and Ggg is Gly or Ser.

In another preferred embodiment of the present invention the peptide has the amino acid sequence of endothelin (Schematic Structure A see below) wherein one or two of the naturally occurring disulfide bridges are replaced by a thioether bond. Therefore the compounds can be shown as described by the schematic structures B [SEQ ID NO:22], C [SEQ ID NO:23] and D [SEQ ID NO:24].

Schematic Structures

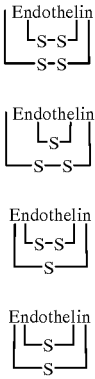

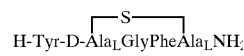
H-Tyr-D-Ala$_L$GlyPheAla$_L$NH$_2$

The preferred peptides of the present invention will have sequentially overlapping thioether bonds as shown above, if the peptide has two thioether linkages. This means that in the amino acid sequence one lanthionine-bridge is located between the two Ala$_L$ rersidues forming the second lanthionine-bridge.

The peptides of the present invention can be used as pharmaceutically active compounds. They can therefore be used in pharmaceutical compositions comprising at least one of the peptides of the present invention.

Pharmaceutical formulations of the peptides comprising the peptides of this invention and a pharmaceutically acceptable carrier are part of this invention. As used herein, the term "pharmaceutically acceptable" carrier encompasses any of the standard pharmaceutical carriers, such as phosphate buffered saline solution, water, emulsions, such as oil/water emulsions, and various types of wetting agents.

The compounds may be administered intravenously and parenterally using well known pharmaceutical carriers or inert diluents. Oral administration is not preferred because the peptides will tend to be degraded by the enzymes of the alimentary tract.

In respect to pharmaceutical compositions containing the peptides disclosed herein, carrier and other ingredients should be such as not to diminish the therapeutic effects of the peptides.

The pharmaceutical compositions of this invention thus will generally comprise an effective amount of the peptide in a suitable pharmaceutically acceptable carrier such as water or alcohols which may contain fillers, stabilizers, wetting agents, emulsifying agents and dispersing agents to name but a few conventional carriers, adjuvant and excipients which may be employed.

The injectable compositions are formulated as shown in the art and may contain appropriate dispersing or wetting agents and suspending agents identical or similar to those mentioned above.

Depending on the nature of the biologically active peptide they can be used in injection solutions, capsules, tablets, ointments, creams, sprays and suppositories.

A representative example of the peptides of the present invention can be produced according to the following procedure described for the enkephalin [SEQ ID NO:1]

The linear peptide chain was assembled on a methylbenzhydrylamine resin using tert-butoxycarbonyl chemistry with the symmetrical anhydride peptide coupling method. A serine residue was preferably incorporated at position 2 and later on converted to dehydroalanine using disuccinimido carbonate. The S-protecting group (fluorenyl methyl) was selectively removed with piperidine.

A slightly basic milieu, preferably 5% piperidine/dimethylformamide, promoted the Michael addition of the SH-group to the double bond. The amino acid analysis showed 48% conversion of serine. A greater excess of the reagent disuccinimido carbonate would have resulted in an increased yield for these two steps. "Low-high HF cleavage" was used to cleave the peptide from the resin and to remove the protecting groups. Purification of the resultant crude product was achieved by preparative RP-HPLC using a gradient acetonitrile-water elution. The material obtained was further purified and desalted by gel filtration on a Sephadex G-15 column (20% acetic acid/water).

The product was identified by amino acid analysis and mass spectrometry. Although the Michael addition is not stereoselective, this reaction resulted in only the (2D, 5L) diastereomer. The other diastereomer expected, (2L, 5L) could not be detected in the reaction mixture. Steric hindrance from the solid support near the SH group may be responsible for the stereoselectivity of the addition reaction. The solid phase synthetic approach allows a rapid assembly of lanthionine-bridged cyclopeptides. FIG. 1 shows schematically the process according to the invention.

Abbreviations Used in Peptide Synthesis Section

Standard abbreviations for amino acids and protecting groups are followed according to the IUPAC-IUB Joint Commission on Biochemical Nomenclature: J. Biol. Chem. 1971, 247, 977. Abbreviations used: Acm, amidocarboxymethyl; Boc, ter-butoxycarbonyl; Bzl, benzyl; DCC, N,N'-dicyclohexylcarbodiimide; DCM, dichloromethane; Dha, dehydroalanine; DMF, dimethylformamide; DIEA, N,N-diisopropylethylamine; DSC, disuccinimidyl carbonate; EtOAc, ethyl acetate; Fm, fluorenylmethyl; Fmoc, fluorenylmethyloxycarbonyl; HOBt 1-hydroxybenztriazole, Ala$_L$, lanthionine; MBHA, methylbenzhydrylamine resin; Pac, phenylacyl; TFA, trifluoroacetic acid; Tmse, trimethylsilylethyl; Z, benzyloxycarbonyl; NCA, N-carboxyanhydrid; Trt, trityl.

Experimental Procedures

All amino acids were of the L-configuration except as indicated. Protected amino acids were purchased from Bachem, Inc. ACS grade solvents (DCM, DMF, acetonitrile) were purchased from Fisher Scientific and purged with nitrogen, then stored over molecular sieves from Sigma. DIEA (Aldrich) was dried over KOH and distilled from ninhydrin. MBHA resin.HCl (Calbiochem) was swollen in DCM and washed with 5% DIEA/DCM followed by DCM before use. TFA, piperidine, DSC (Aldrich) and DCC (Fluka) were used without further purification. Silica gel for flash chromatography was purchased from Baker.

Peptides were analyzed on precoated silica gel 60F-254 plates (Merck) using (A) chloroform:methanol:acetic acid, 65:35:1; (B) butanol:acetic acid:water, 4:1:5—upper phase. Compounds were visualized by UV, ninhydrin, chlorine/o-tolidine and KMnO$_4$ solution. RP-HPLC analyses were performed on a Waters (Model 510 and Waters 484 detector) instrument with a C-18 analytical column.

There is, however, another synthetic method for the production of peptides. It is often desirable to have diastereomeric peptide analogs. The use of diastereomeric mixture of lanthionine units can provide appropriate diastereomeric analogs, separable by chromatography (HPLC). By such routes, two (or four) analogs can be prepared by a single synthetic process. The simultaneous application of the benzyloxycarbonyl, t-butyloxycarbonyl and phenacyl (or methyl, trimethylsilylethyl, etc.) groups defines the synthetic strategy of this invention to prepare

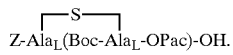
Z-Ala$_L$(Boc-Ala$_L$-OPac)-OH.

A new application of the PCOR method (Peptide Cyclization on an Oxime Resin) can provide the new cyclic segment containing a defined lanthionine bridge (Scheme 2), where the chain can be elongated at both termini. The process without a lanthionine bridge has been described in more detail by Osapay et al. in J. Am. Chem. Soc. 1990, 112, p. 6046–6051 and Tet. Lett. 1990, 31, p. 6121–6124. The final deprotection step followed by chromatographic purification yields the desired compounds.

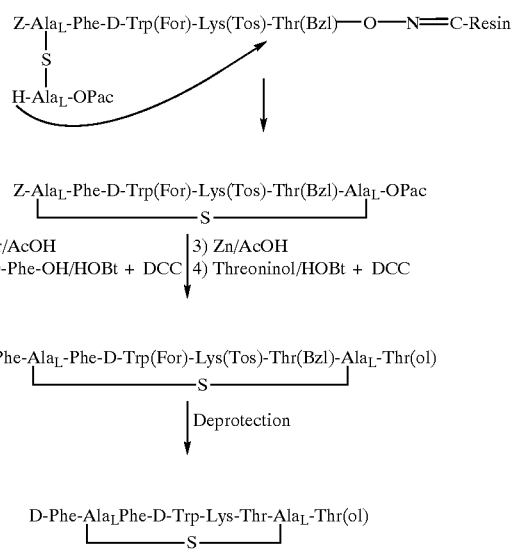

Another highly promising pathway involves the synthesis of two protected intermediates, followed by coupling of the two components in generating an optically pure lanthionine. This is proceeded by the synthesis of both the protected serine β-lactone (Arnold et al. J. Am. Chem. Soc. 1988, 110, p. 2237–2241) and the protected cysteine. The latter compound acts as a nucleophile in opening the lactone ring at the site of the methylene group (see Scheme 3).

Scheme 1
Synthesis of Protected Lanthionine from Dehydroalanine

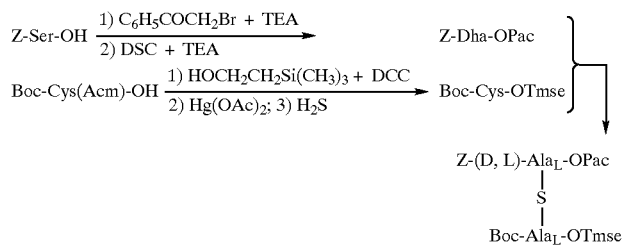

Scheme 2
Synthesis of Lanthionine-sandostatin
Utilizing Cyclization on an Oxime Resin Boc-Thr(Bzl)-O—N═C-Resin 1) Chain elongation by BOP couplings | 2) TFA/DCM; 3) DIEA Scheme 2B
Synthesis of Lanthionine-SRIF[1–14]

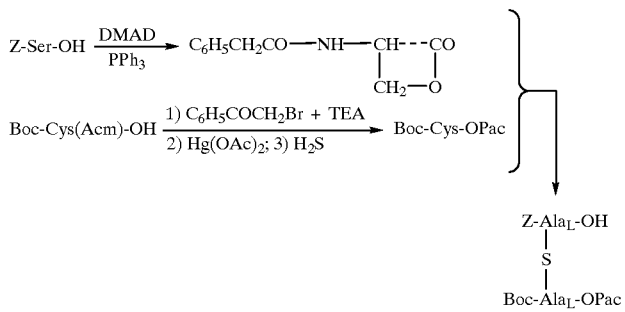

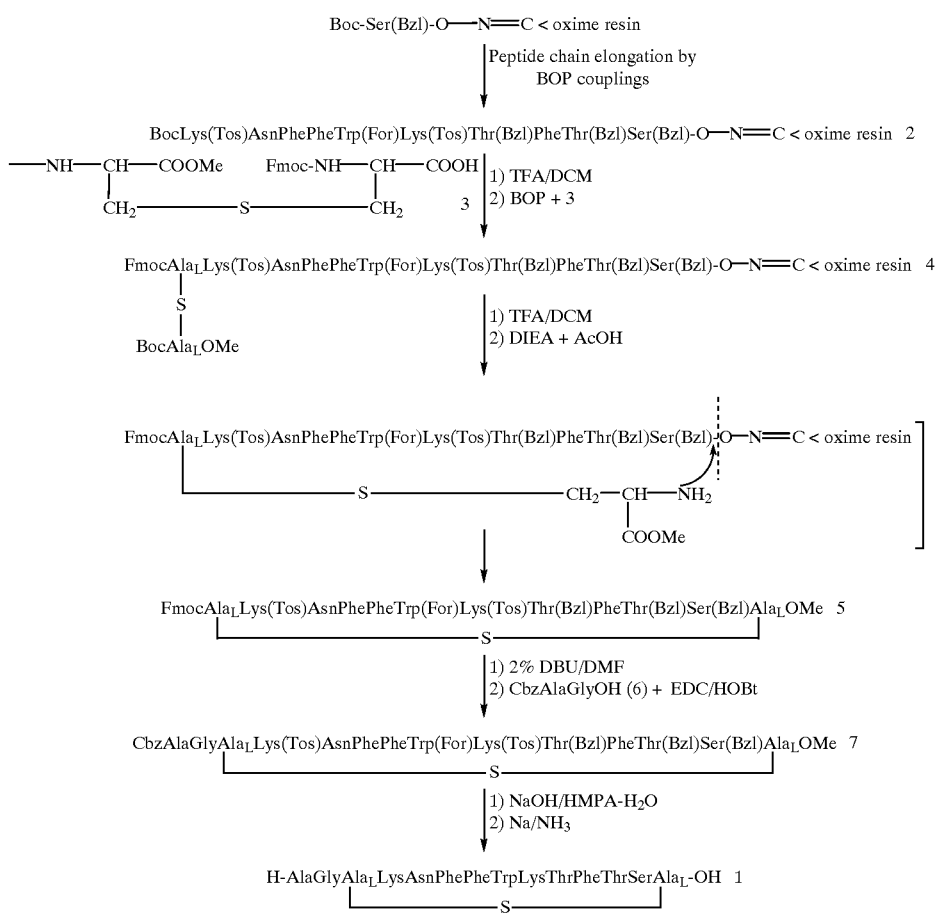

Figure 2:
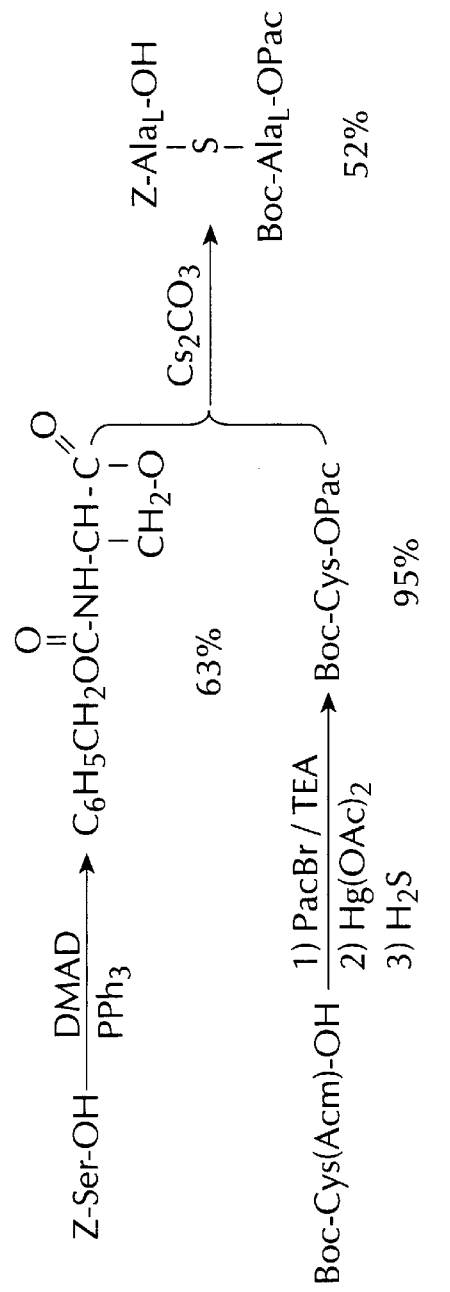

The β-lactone method is shown in FIG. 2 wherein also the obtainable yields are given.

Furthermore another route for the synthesis of the protected lanthionine is disclosed where reactions proceed with retention of configuration. This lanthionine derivative is prepared through the ring opening of an aziridine derivative (Wakamiya et al., Bull. Chem. Soc. Jpn., 1982, 55, 3878–3881) by a nucleophile, namely cysteine or any appropriate SH-containing amino acid (Scheme 4).

Scheme 4
Synthesis of Protected Lanthionine from Aziridine Derivatives

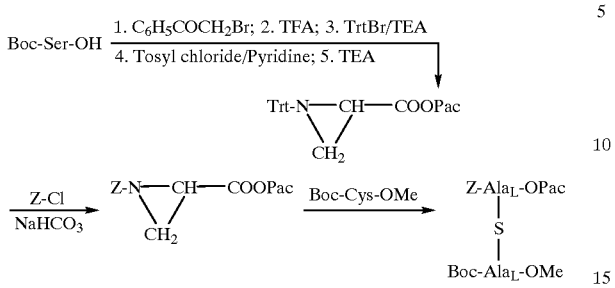

Figure 3:

The Aziridine method is shown in FIG. 3 wherein also the yields obtainable by said method are given.

Preparation of Lanthionine-opioids

As will be shown later, all of the lanthionine opioids synthesized are superactive both at the μ- and δ-receptor. To investigate structural or pharmacochemical aspects of this new class of opioids, analogs can be synthesized in order to carry out bioassays and conformational analyses of the resulting molecules. Various peptidic or peptidomimetic units can be incorporated into cyclic enkephalin and dermorphin-deltorphin structures including:

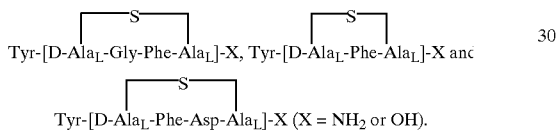

The incorporation of methyl group(s) at the β-carbon(s) and effects of chirality at the two main chain units of the lanthionine residue can also be included.

Thus the synthesis of β-methyl lanthionines and β-dimethyl lanthionine results in modifications, which are expected to lead to substantial differences in bioactivity profiles for closely related target molecules. Thus, critical information about the "bioactive conformations" of the analogs can be obtained. In addition, specific residues such as the Gly in the

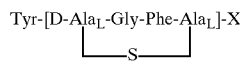

and the Asp of

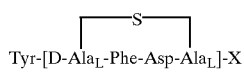

can be modified with natural and unnatural amino acids. This family of opioids are most promising for obtaining novel and clinically useful opioid drugs.

Lanthionine-somatostatins

New lanthionine-somatostatin derivatives can be synthesized. First, the cyclic segment with a monosulfide bridge of somatostatin or "key-hexapeptide" (Scheme 2) or other analogs of somatostatin according to the definition of $R_1$ on a Kaiser-oxime resin has to be prepared. It will be elongated at both termini (D-Phe at the N-terminus and threoninol at the C-terminus) to obtain for example the lanthionine analog of Sandostatin. The same synthetic strategy can be used for the preparation of the lanthionine analog of the native somatostatin tetradecapeptide. Potency and receptor selectivity of both target molecules are promising.

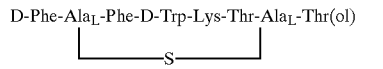

Lanthionine-sandostatin

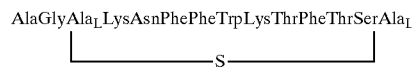

Lanthionine-somatostatin [SEQ ID NO:2]
Lanthionine-calcitonins [SEQ ID NO:16–21]

It is possible to incorporate the lanthionine as the replacement of the cysteine-cysteine disulfide bridge in the N-terminal loop. The loop can be prepared via the PCOR method (Scheme 5).

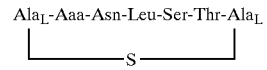

Human and rat calcitonins: Aaa = Gly
Salmon and eel calcitonins: Aaa = Ser

Scheme 5
Synthesis of Loops for Lanthionine-calcitonins Utilizing Cyclization on an Oxime Resin

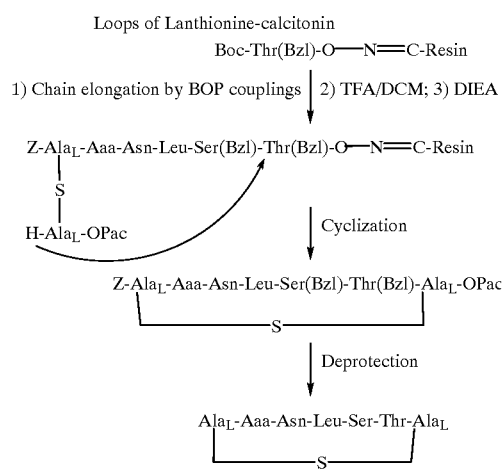

Human and rat calcitonins: Aaa = Gly
Salmon and eel calcitonins: Aaa = Ser

The elongation at the C-terminus to get the final calcitonin-analog can be performed by normal classical fragment condensations or by the strategy shown later in the paragraph of lanthionine-oxytocin and -vasopressin synthesis (Scheme 6).

Lanthionine-oxytocins and Lanthionine-vasopressins

The incorporation of a lanthionine bridge to replace the existing disulfide bridge found in natural oxytocin (OT) and vasopressin (VP) is another example. This can be accomplished by the synthesis of the lanthionine component prior to its incorporation in the peptide sequence (Scheme 6).

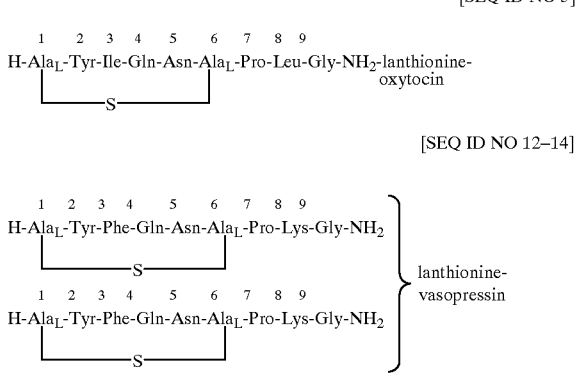

[SEQ ID NO 5]

lanthionine-oxytocin

[SEQ ID NO 12–14]

lanthionine-vasopressin

Scheme 6
Synthesis of Lanthionine-oxytocins/Lanthionine-vasopressins

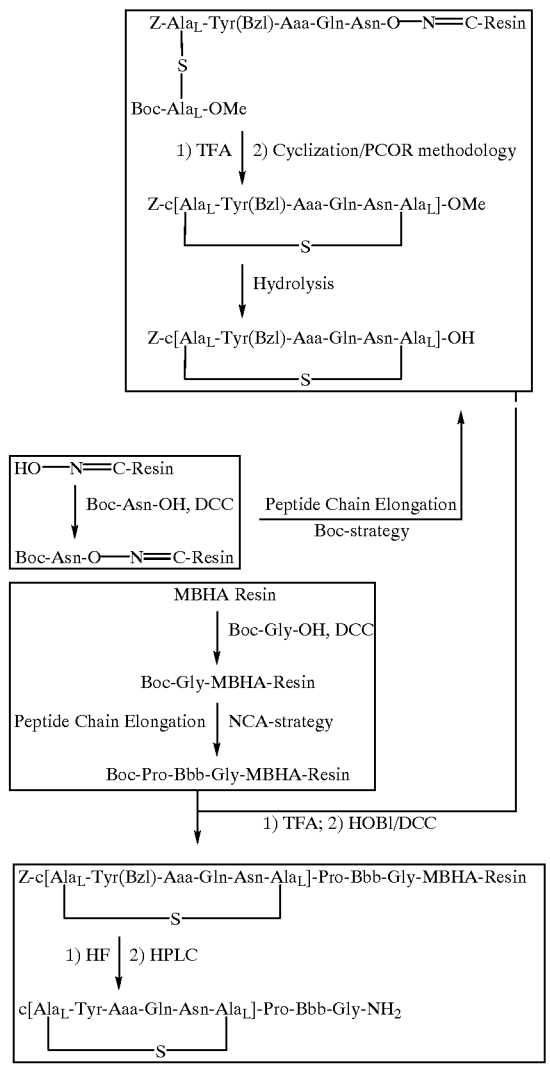

I   Oxytocin: Aaa = Ile; Bbb = Leu
II  Lysine-Vasopressin: Aaa = Phe; Bbb = Lys(2Cl-Z)
III Arginine-Vasopressin: Aaa = Phe; Bbb = Arg(NO$_2$)

The following examples illustrate the present invention without limiting the scope of the invention thereto.

EXAMPLE 1 a) Preparation of Z-Tyr(Bzl)-Ser-Gly-Phe-Cys(Fm)-MBHA (1)

Methyl benzhydrylamine resin (3 g) was reacted with Boc-Cys(Fm)OH (1.0 g, 2.5 mmol) and DCC (0.52 g, 2.5 mmol) in DCM (30 mL) for 3 hr at room temperature in an SPPS vessel. The remaining amino groups were capped by acetylation. The resulting Boc-Cys(Fm)-MBHA resin (substitution level 0.36 mmol/g, based on picric acid titration) was then deprotected with 30% TFA/DCM (v/v) and neutralized with 1% DIEA/DCM (v/v) solution. The peptide chain was then assembled by consecutive addition of the symmetrical anhydrides (2.5 equiv.) of BocPheOH, BocGlyOH, BocSerOH, and ZTyr(Bzl)OH as well as deprotection steps. The completeness of coupling was monitored by the Kaiser test. Coupling of ZTyr(Bzl)OH was repeated with 1 molar equivalent reagent. Yield 1.06 mmol (84%) peptide based on Gly; amino acid analysis; $Cys_{(1)}$ $Gly_{1.00}Phe_{0.86}Ser_{1.42}Tyr_{1.22}$.

b) Preparation of (3)

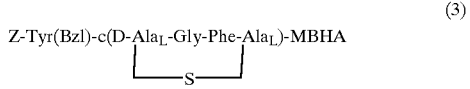

The protected peptidyl MBHA resin (1, 1.06 mmol) in the SPPS vessel was swollen and then suspended in DCM (20 mL). A solution of DSC (387 mg, 1.51 mmol) in acetonitrile (10 mL) was added to the reaction mixture followed by a 5% DIEA/DCM solution (5.22 mL, 1.5 mmol DIEA). The reaction was allowed to proceed for 4 hr, shaking at room temperature in a nitrogen atmosphere. The reaction mixture was drained and the solid phase was washed with DCM (4×). The product (2) was treated with a solution of 20% piperidine/DMF solution (20 mL, v/v, 2×50 min.) and shaken in a 5% piperidine/DMF-DCM solution (40 mL, 1/1, v/v) overnight. The solution phase was drained and the resin was washed with DMF (1×), DCM (2×) and EtOH (2×) and dried. Yield 3.7 g.

c) Preparation of (4)

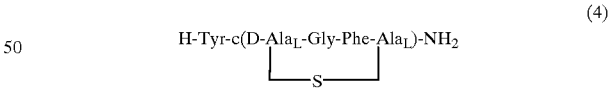

The peptidyl resin (3, 1.0 g) was treated with anhydrous HF (20 mL) at 0° C. in the presence of anisole (1 mL) for 1 hr in a teflon HF apparatus. After removal of volatile components the remaining material was washed with EtOAc (2×20 mL) and the product was extracted with acetic acid followed by 10% acetic acid/water solution. The combined extracts were freeze-dried (yield 200 mg). This material was purified by preparative RP-HPLC on a Vydac C-18 column (1.0×25 cm) eluted with 0.1% TFA in acetonitrile/water. A linear gradient from 15% to 22% acetonitrile over 12 min with a flow rate of 10 mL/min was employed. The appropriate fractions were lyophilized to give a solid product (yield 87 mg). Finally, 30 mg of the product was subjected to gel permeation chromatography (1.5×100 cm Sephadex G-15 eluted with 20% acetic acid). The peptide fractions were pooled and lyophilized. Yield 16 mg (24% calculated for compound 1). $R_F(A)$ 0.44; $R_F(B)$ 0.49. FAB-MS m/e= 557 (M+1). Amino acid analysis $Gly_{1.00}Ala_L$-S-$Ala_{L1.1}Phe_{0.99}Tyr_{0.95}$.

EXAMPLE 2

Figure 4:
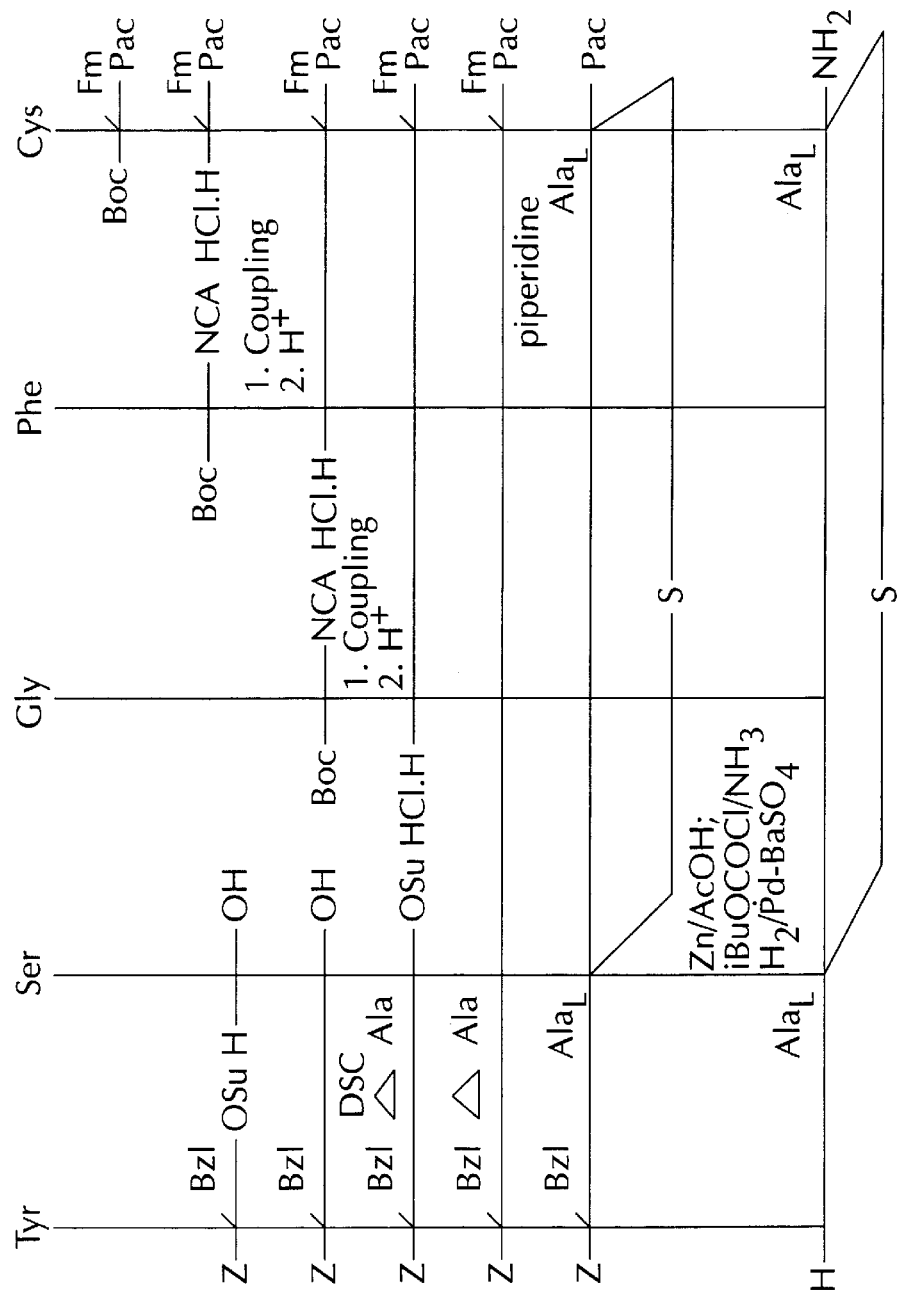

FIG. 4 shows schematically the synthesis of lanthionine-enkephalin in solution. Other general methods for chemical synthesis can be followed using mixed anhydrides, carbodiimides, active esters and other coupling procedures. Preferred solvents are $CH_2Cl_2$ and DMF. Cleavages are following standard selective reactions. Purification follows well-known extractions, precipitations and chromatographic methods.

EXAMPLE 3

The lanthionine-enkephalin was also synthesized by the preferred Fmoc-NCA-Strategy by using the following steps:
(1) Deprotection (20% piperidine/DMF) 7 min 30 mL/min
(2) Wash (DMF) 5 min 30 mL/min
(3) Coupling (see below) 20 min 30 mL/min
(4) Wash (DMF) 5 min 30 mL/min
(5) Repeat steps 1–4

The coupling was performed as follows:
1: 3 eq. 20 min; #2: 1 eq.+DIEA 20 min
(a) Fmoc-Phe-NCA,
(b) Fmoc-Gly-NCA,
(c) Fmoc-Ser-OH/DCC,
(d) Fmoc-Tyr(Bzl)-NCA.

In the case of peptide chain elongation by the Fmoc-strategy the —SH group of cystein was blocked with a Trt group.

EXAMPLE 4

The preparation of lanthionine-bridged cyclic peptide fragments is demonstrated by the following preparations:

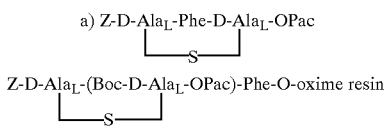

(1.0 g, 187 μmol peptide on resin) synthesized by regular solid phase synthetic method was swollen in DCM (10 mL) in a solid-phase peptide synthesis vessel. The Boc group was removed with 25% TFA/DCM, shaking the reaction vessel for 30 min. The peptidyl resin was then drained and washed (10 mL/wash) with DCM (2×), i-PrOH (1×), DCM (2×), i-PrOH (1×), and DCM (2×). The amino group was neutralized by treating the peptidyl resin with 5% DIEA in DCM (2×1 min.) and then washing with DCM (2×). The cyclization reaction was then carried out by shaking the peptidyl resin in DCM/DMF (1:1, v/v, 10 mL) in the presence of 10 equiv. AcOH at RT for 72 h. The cyclic peptide product was collected from the reaction vessel by draining and then washing the resin with DMF (3×). These solutions were combined and evaporated to a reduced volume, and then washed with water, 0.1 N HCl, 5% $NaHCO_3$, and brine. The solvent was then evaporated and the crude product was purified by silica gel flash chromatography (2×20 cm, ethyl acetate-hexanes 1/1). The appropriate fractions were pooled and the solvent was evaporated. The pure solidified product was recrystallized from methanol/ether. Yield 75.0 mg (68%); mp 241–244° C. (decomp); $R_F$(EtOAc/hexanes=2/1) 0.42; FAB-MS m/e=590 ($MH^+$); theoretical 590.

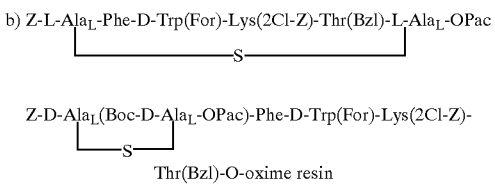

(100 mg, 6.0 μmol peptide on resin) synthesized by regular solid phase synthetic method was swollen in DCM (1.0 mL) in a solid-phase peptide synthesis vessel. The Boc group was removed with 25% TFA/DCM, shaking the reaction vessel for 30 min. The peptidyl resin was then drained and washed (1.0 mL/wash) with DCM (2×), i-PrOH (1×), DCM (2×), i-PrOH (1×), and DCM (2×). The amino group was neutralized by treating the peptidyl resin with 2.5% DIEA in DCM (2×1 min.) and then washing with DCM (2×). The cyclization reaction was then carried out by shaking the peptidyl resin in DCM/DMF (1:2, v/v, 1.0 mL) in the presence of 10 equiv. AcOH at RT for 72 h. The cyclic peptide product was collected from the reaction vessel by draining and then washing the resin with DMF (3×). These solutions were combined and evaporated and the crude product was purified by RP-HPLC on a Vydac C-18 column (1.0×25 cm) using 0.1% TFA in acetonitrile water. A linear gradient from 50 to 80% acetonitrile over 15 min., with a flow rate of 4 mL/min., was employed. The product was eluted at 61% acetonitrile and lyophilized to give a solid product. Yield 0.9 mg (24%); $R_F$($CHCl_3$/MeOH/AcOH=18/1.5/1) 0.54; FAB-MS m/e=1, 293 ($MH^+$); theoretical 1,293.

EXAMPLE 5

Comparative examples showing the superior biological activity of compounds with the thioether bond compound compared with the compound having the disulfide bridge:
Bioassays Using Isolated Organ Preparations All of these assays represent standard procedures which have been well described in the literature.

(1) The GPI (guinea pig ileum) assay was performed according to a modified version of a procedure first developed by Paton. Male guinea pigs (300–450 g) were killed by a blow on the skull and exsanguinated. A 2–3 cm segment of ileum not less than 10 cm from the ileocecal junction was mounted in a 20 ml organ bath. The bath contained Krebs' solution of the following composition (in millimolar concentrations): NaCl, 150; KCl, 4.3; $CaCl_2$, 1.25; $MgCl_2$, 1.0; $NaH_2PO_4.H_2O$, 1.7; $NaHCO_3$, 25.0; glucose, 11.0. The temperature was maintained at 37° C. and the solution was bubbled with 95% $O_2$,% $CO_2$. A GRASS E 2B electrode was used as anode with the 1.5 cm platinum wire entirely enclosed within the lumen. The other end of the preparation was tied over a piece of stiff polyethylene tubing (4 cm, 2.5 mm O.D) which projects out of the bath solution and was tied to the strain gauge. Another GRASS E 2B electrode was placed about 5 mm from the intestine and parallel to it to achieve transmural stimulation. Single pulses of 4 msec during were delivered by a Harvard apparatus stimulator at a frequency of 10 min$^{-1}$. Voltages in the range from 3 to 6 V were applied in order to obtain maximal response. Isometric contractions of the ileum were recorded via a Harvard isometric force transducer on a Harvard apparatus biograph which has been calibrated to produce a pen displacement of 1 cm per tension change of 1 g. The results were standardized by expressing the reduction in tension obtained at each dose level as a -percentage of the mean tension produced by at least ten preceding control stimulations. Semilogarithmic plots of percent inhibition as a function of peptide concentration permit the determination of IC50-values which were taken as the intercept of 50% inhibition.

(2) The MVD (mouse vas deference) assay was performed essentially as described by Henderson. Briefly, adult, male albino mice (Swiss Webster 30–50 g) are killed by cervical dislocation and the vas deferentia are dissected out. After removal of extraneous fat and connective tissue, the vas is stripped of its associated blood vessel and the somen is gently expressed from the lumen. The vas is then mounted under 0.5 g tension in a 5 ml organ bath containing warmed (37° C.), oxygenated (95% $O_2$, 5% $CO_2$%)), $Mg^{2+}$-free Krebs solutions of the following composition [mM]: NaCl, 118; $CaCl_2$, 2.54; KCl, 4.75; $KH_2PO_4$, 1.19; $NaHCO_3$, 25; glucose, 11; L-tyrosine, 0.2. A modified Harvard apparatus stimulator is used to deliver repetitive field stimulation through platinum wire ring electrodes at the top and bottom of the bath, consisting of twin, rectangular pulses (80 V, 0.15 Hz, 10-ms delay, 1.0-ms duration). Contractions of the muscle are recorded via a Hewlett-Packard Model FTA-l-l force transducer connected to a Hewlett-Packard 7702B recorder. Deterimnation of the resuction in the twitch length at various doses permits the construction of log dose-response curves and the determination of IC50 values.

Example 6

Using protocols described by Shiller et al., Biochem. Biophys. Res. Commun. 1983, 115, p. 864–870, we compared the half-lives of three compounds: Leu$^5$-enkephalin, disulfide-enkephalin, and lanthionine-enkephalin. As indicated in Table 2, the lanthionine-enkephalin is much more stable than the other two compounds.

TABLE 2

Enzymatic Degradation of Enkephalin Analogs

| Analog | t½ (min) |
| --- | --- |
| Lanthionine-enkephalin | 1223 |
| Disulfide-enkephalin | 332 |
| Leu$^5$-enkephalin | 30 |

EXAMPLE 7

The lanthionine opioid is highly active in the in vitro and in vivo tests (Table 3). In vivo bioactivity was determined using the rat hot plate test after intrathecal dosages.

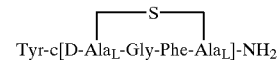

shows 37 times higher bioactivity than morphine and twice the activity of DCLCE (Table 3). In the same tests, [Leu$^5$]-enkephalin shows only 40–50% of full agonistic activity after 100 pg dosage in the in vitro assays using GPI and MVD preparations. The lanthionine opioid exhibits 400 times greater bioactivity at the GPI ($\mu$-receptor) and 20 times greater bioactivity at the MVD ($\delta$-receptor) than [Leu$^5$]-

TABLE 1

Inhibitory Potency and Selectivity of Lanthionine and Disulfide-Bridged Enkephalin Analogs in GPI (guinea pig ilium) and MVD (mouse vas deferens) Bioassays Adequate to $\mu$ and $\delta$ Receptor Binding Affinities, Respectively, and Rat Hot-plate in vivo Test

| Structures | GPI IC$_{50}$ (nM) | MVD IC$_{50}$ (nM) | GPI/MVD IC$_{50}$ (nM) | in vivo IC$_{50}$ (nM) | $\delta$-Binding$^a$ IC$_{50}$ (nM) |
| --- | --- | --- | --- | --- | --- |
| Tyr-c[D-Ala$_L$-Gly-Phe-L-Ala$_L$]-NH$_2$ | 0.62 | 0.54 | 1.13 | 0.11 | 7 |
| Tyr-c[D-Ala$_L$-Gly-Phe-D-Ala$_L$]-NH$_2$ | 1.67 | 1.67 | 1.0 | 0.11 | N/D |
| Tyr-c[D-Ala$_L$-Gly-Phe-L-Ala$_L$]-OH | 0.45 | 0.16 | 2.85 | 0.19 | 1 |
| Tyr-c[D-Cys-Gly-Phe-L-Cys]-NH$_2$ | 1.51 | 0.76 | 1.99 | 0.24 | N/D |
| Tyr-c[D-Cys-Gly-Phe-D-Cys]-NH$_2$ | 0.78 | 0.30 | 2.61 | 0.29 | N/D |
| Tyr-c[D-Cys-Gly-Phe-L-Cys]-OH | 3.06 | 0.19 | 16.1 | N/D | N/D |
| Tyr-c[D-Val$_L$-Gly-Phe-L-Ala$_L$]-OMe | 88.1 | 3.65 | 24.1 | N/D | N/D |
| Tyr-c[D-Val$_L$-Gly-Phe-L-Ala$_L$]-OH | 39.0 | 0.27 | 143 | N/D | N/D |
| Tyr-c[D-Val$_L$-Gly-Phe-D-Ala$_L$]-OH | 535 | 1.51 | 354.3 | N/D | N/D |
| Tyr-c[D-Pen-Gly-Phe-D-Pen]-OH | 7300 | 4.1 | 1800 | 130 | 78 |
| Tyr-Gly-Gly-Phe-Leu | 246 | 11.4 | 21.6 | >180$^b$ | N/D |
| Morphine | 58.6 | 644.0 | 0.09 | 15 | >1000 |

$^a$replacements of 3H-naltrindole;
$^b$40% of the maximum activity at 180 nmol dosage Table 1 shows that the compound according to the invention which has a thioether bond is in both methods, particularily in the most relevant GPI test, more potent than the corresponding —S—S— compound.

enkephalin. These values are higher than those of its disulfide bridged counterpart, DCDCE. The lanthionine analog does not show a preference for the $\mu$- or the $\delta$-receptor. The IC$_{50}$ ratio (MVD/GPI) is 0.9.

TABLE 3

Potencies of Lanthionine and Disulfide-bridged Somatostatin Analogs to Inhibit Radioligand Binding to Cloned somatostatin Receptors [SSTR2 and SSTR4]*

| Structures | Binding Constants [IC$_{50}$ (nM)] | |
| --- | --- | --- |
| | SSTR2 Receptor | SSTR4 Receptor |
| H-D-Phe-c[Ala$_L$Phe-D-Trp-Lys-Thr-Ala$_L$]-OH | 0 | 500 |
| H-D-Phe-c[Ala$_L$Phe-D-Trp-Lys-Thr-Ala$_L$]-Thr-ol | 5.00 | 1.00 |
| H-D-Phe-c[Ala$_L$Phe-D-Trp-Lys-Thr-Ala$_L$]-Thr-NH$_2$ | 10.0 | 0.50 |
| Sandostatin | | |
| H-D-Phe-c[Ala$_L$Phe-D-Trp-Lys-Thr-Ala$_L$]-Thr-ol | 2.4 | 0.57 |
| c[Ala$_L^3$, Ala$_L^{14}$]-Somatostatin-14 | 0.3 | — |
| Somatostatin-14 | 0.28 | 0.86 |

*measured according to K. Raynor et al. (1993) Mol. Pharmacol. 43, 838–844, and 44, 385–392

Although the lanthionine-enkephalins according to the invention possess superactivity, they do not seem to have high receptor selectivity. To imporoive thier selectivity, it is possible to introduce one or more alkyl (methy) group(s) in β positions) of the lanthionine segment.

In this case at least one of $R_4$, $R_5$, $R_7$, and $R_8$ may be alkyl (methyl).

The two lanthionine octapeptides in Scheme 3 are highly potent on both SSTR2 and SSTR4 receptors. They have similar affinities to SSTR4 as sandostatin but their affinities for SSTR2 are slightly decreased. By comparing the IC$_{50}$ values for SSTR2/SSTR4 receptors, the disulfide and monosulfide bridged octapeptide alcohols are practically the same. On the contrary, the octapeptide amide has a four times higher selectivity for SSTR4 because its affinity to SSTR2 is decreased. The lanthionine analog of SRIF 14 shows the same binding affinity to SSTR2 as the natural disulfide bridged peptide.

Preparation A

Preparation of Lanthionine Building Blocks for Syntheses of Lanthionine Peptides 1) Z-Ala$_L$(Boc-Ala$_L$-OPac)-OH Benzyloxycarbonyl-serine lactone (1.1 g, 5 mmol) and t-butyloxycarbonyl-cysteine phenacyl ester (2.04 g, 6 mmol) are dissolved in DMF (25 ml) and cesium carbonate (0.97 g, 3 mmol) is added to the solution. The reaction mixture is stirred at room temperature for one hour in nitrogen atmosphere, the solvent is removed under reduced pressure. The residue is dissolved in a mixture of 10% NaHSO$_4$ and ethyl acetate. The organic phase is washed with water, dried with sodium sulfate and the solvent is removed under reduced pressure. The crude product is purified on silica gel column with a solvent system of chloroform-methanol (10/1, v/v). The fractions containing the product are combined and the solvent removed. The product is a white foam.

Yield: 1.46 g (52%); R$_f$(CHCl$_3$/MeOH=10/1)=0.20; FAB-MS (m/e)=561 (MH)$^+$.

2) Z-Ala$_L$(Trt-Ala$_L$-OMe)-OH

The compound can be prepared according to the literature: Photaki, I., Samouilidis, I., Caranikas, S. and Zervas, L. *J.Chem.Soc.Perkin I.*, (1979) 2599.

3) Z-Ala$_L$(Boc-Ala$_L$-OMe)-OPac

Benzyloxycarbonyl-aziridine phenacyl ester (111.7 mg, 0.33 mmol) and t-butyloxycarbonyl-cysteine methyl ester (106.1 mg, 0.45 mmol) are dissolved in DCM (2 ml). BF$_3$.Et$_2$O (2 drops) is added to the solution at room temperature, and the reaction stirred under nitrogen. After five days, the solvent is removed under reduced pressure. The residue is then dissolved in ethyl acetate, and washed sequentially with 10% NaHCO$_3$, water, and brine. Ethyl acetate layer is dried over magnesium sulfate and then removed under reduced pressure. The crude product is purified on a silica gel column with a solvent system of ethyl acetate-hexane (1:2, v/v). Compound is a white powder from ethyl acetate-hexane.

Yield: 82 mg (43.2%); m.p. 93.5–94.5° C.; R$_f$(EtOAc/Hexane=1/2)=0.3; FAB-MS (m/e)=575(MH)+.

Found: C, 58.45; H, 5.99; N, 4.82; S, 5.46%. Calculated: C, 58.51; H, 5.98; N, 4.88; S, 5.58%.

Preparation B

Syntheses of Lanthionine-somatostatin Analogs

1) Z-c[Ala$_L$Phe-D-Trp(For)Lys(Tos)Thr(Bzl)Ala$_L$)-OMe

BocThr(Bzl)-oxime resin (5.4 g, substitution level: 0.26 mmol/g based on picric acid titration) was deprotected with 25% TFA/DCM (v/v) and neutralized by 5% DIEA/DCM (v/v). The peptide chain was then assembled by consecutive addition of 2.5 equiv. BOB ester of BocLys(Tos)OH, Boc-D-Trp(For)OH, BocPheOH and ZAla$_L$(TrtAla$_L$OMe)OH as well as deprotection steps. After the Trt group was removed with 25% TFA/DCM (v/v) the peptidyl resin was washed and neutralized according to the standard oxime resin protocol. The cyclization reaction was carried out by shaking the peptidyl resin in DMF-DCM (100 mL, 2/1 v/v) in the presence of 10 equiv. of acetic acid at room temperature for 24 hr. The cyclic peptide product was obtained from the filtrate of the reaction mixture: The solvent was removed in reduced pressure and the product was precipitated from a mixture of DMF-water.

Yield: 1.07 g (65%), R$_f$(CHCl$_3$/MeOH/AcOH)=0.79, RP-HPLC: R$_T$=23.5 min (Vydac C-18 semipreparative column; eluent: acetonitrile-water mixture containing 0.1% TFA; conditions: linear gradient from 30 to 90% of acetonitrile during 30 min.). FAB-MS: m/e 1.173 (M+H$^+$).

2) Z-D-Phe-c[Ala$_L$Phe-D-Trp(For)Lys(Tos)ThrAla$_L$)-OMe

The protected hexapeptide (1, 1.0 g, 0.85 mmol) was partially deprotected with 33% HBr/AcOH (6 mL, v/v) at 0° C. for 10 min and at room temperature for 50 min. Abs. ether (50 mL) was given to the reaction mixture and kept at 0 C for 1 hr. The product was filtered and dried.

Yield: 0.92 g, R$_f$(EtOAc/BuOH/AcOH/H$_2$O)=0.93, Z-D-PheOH (3.2 g, 3.29 mmol) and HOBt.H$_2$O (0.89 g, 6.58 mmol) were dissolved in DMF (5 mL), cooled to 0° C. and EDC 0.69 g, 3.62 mmol), DIEA (1.91 ml, 11.0 mmol) and the HBr salt of the above peptide (0.91 g, 0.82 mmol) were given to the reaction mixture. After being stirred for 1 hr at 0° C. and at room temperature for overnight the product was precipitated by addition of water. The crude product was filtered, washed with 0.5 N HCl, 5% NaHCO$_3$ and water, then recrystallized from DMF-ether.

Yield: 0.9 g (86%), RP-HPLC: R$_T$=15.3 min (same column and eluent written above; conditions: linear gradient from 50 to 75% of acetonitrile during 20 min). FAB-MS: m/e 1,231 (M+H$^+$).

3) Z-D-Phe-c[Ala$_L$Phe-D-TrpLys(Tos)ThrAla$_L$)-ThrNH$_2$

The protected heptapeptide (2, 0.3 g, 0.24 mmol) in DMF (6 mL) was stirred with N$_2$H$_4$.H$_2$O (0.6 mL) overnight under nitrogen atmosphere. The solvent was partly removed under reduced pressure then water was added to the reaction mixture. The precipitated product was filtered and dried.

Yield: 220 mg, RP-HPLC: R$_T$=10.9 min (same conditions as described for compound 2). FAB-MS; m/e 1,204 (M+H$^+$). To a solution of this material (180 mg), 0.15 mmol) in DMF (2 mL) cooled to −15° C., 4N HCl/dioxane (0.225 mL) and t-butyl nitrite (0.042 mL 0.35 mmol) were added. After being stirred for 25 min at the same temperature HCl.H-Thr-NH$_2$ (0.139 g, 0.9 mmol) and DIEA (0.195 mL, 1.25 mmol) were added to the reaction mixture. After a further 1 hr stirring at −15° C. and 48 hr at 4° C. the mixture was diluted with water. The precipitated product was filtered, washed with 1N HCl, 5% NaHCO$_3$ and dried. The crude material was recrystallized from DMF-ether.

Yield: 192 mg, RP-HPLC: R$_T$=21.5 min (same column and eluent written above; conditions: linear gradient from 50 to 100% of acetonitrile during 25 min). FAB-MS; m/e 1,290 (M+H$^+$) and 1,312 (M+Na$^+$).

4) H-c(Ala$_L$Phe-D-TrpLysThrAla$_L$)-OH

The protected hexapeptide (1, 58.6 mg, 0.05 mmol) was dissolved in hexamethylphosphoramide (1.25 mL) cooled to 15° C., 0.5 N NaOH (0.5 mL) was added dropwise over 30 min. The reaction mixture was stirred for further 30 min at this temperature, then and diluted with water (15 mL) acidified to pH 2.5 with 2.5 N HCl at 0° C. After being kept for 1 hr at this temperature the product was filtered, dried and recrystallized from DMF-ether. Yield: 110 mg, RP-HPLC: R$_T$=13.7 min (same conditions as described for compound 2). FAB-MS: m/e 1,131 (M+H$^+$). This material was deprotected with sodium (23 mg) in liquid ammonia (40 mL). After removal of the ammonia the rest was dissolved in water (2 mL) and the pH was adjusted to 5 with acetic acid. The solution was subjected to gel permeation chromatography (1.5×75 cm Sephadex G-10 eluted with 10% acetic acid) followed by RP-HPLC purification on a Vydac C-18 semipreparative column eluted with isocratic 22% acetonitrile/water containing 0.1% TFA. The pure peptide fractions were pooled and lyophilized.

Yield: 19 mg (51%), RP-HPLC: R$_T$=14.0 min (conditions above). FAB-MS; m/e 753 (M+H$^+$).

5) H-D-Phe-c[Ala$_L$Phe-D-TrpLysThrAla$_L$)-ThrNH$_2$

The protected octapeptide (3, 100 mg, 0.077 mmol) was deprotected by sodium (46 mg) in liquid ammonia (75 mL). After removal of the ammonia the residue was desalted by gel permeation chromatography (1.5×75 cm Sephadex G-10 eluted with 10% acetic acid) followed by RP-HPLC purification on a Vydac C-18 semipreparative column. The pure peptide fractions were pooled and lyophilized.

What is claimed is:

1. A lanthionine-bridged peptide of the formula:

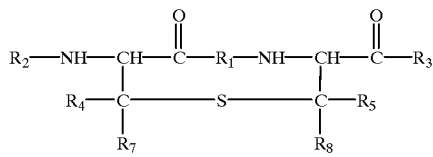

wherein $R_1$ represents Gly-Phe;

$R_2$ represents an amino acid selected from the group consisting of D-Phe, D-β-Nal, Tyr, TrpNH$_2$, ThrNH$_2$ and Thr(ol); or represents H, acyl or aracyl with 2 to 12 carbon atoms; or represents an amino acid sequence selected from the group consisting of Pro-Arg-Gly and Pro-Leu-Gly;

$R_3$ represents an amino acid selected from the group consisting of D-Phe, D-β-Nal, Tyr, TrpNH$_2$, ThrNH$_2$ and Thr(ol); or represents OH or NH$_2$; or represents an amino acid sequence selected from the group consisting of Pro-Arg-Gly and Pro-Leu-Gly; or

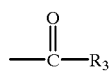

can be replaced by CH$_2$OH; and $R_4$, $R_5$, $R_7$ and $R_8$ independently represent hydrogen or a methyl group.

2. The peptide according to claim 1, wherein $R_2$ and $R_3$ are individually selected from the group consisting of Pro-Arg-Gly and Pro-Leu-Gly.

3. The peptide according to claim 1, which has the formula:

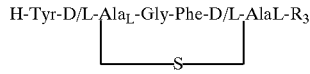

where $R_3$ represents OH or NH$_2$.

4. The peptide according to claim 1, which has the formula:

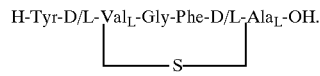

5. The peptide according to claim 4, which has the formula:

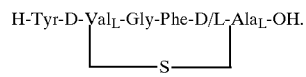

6. A pharmaceutical composition comprising at least one peptide according to claim 1 in a physiologically acceptable carrier.

7. A pharmaceutical composition comprising at least one peptide according to claim 2 in a physiologically acceptable carrier.

8. A pharmaceutical composition comprising at least one peptide according to claim 3 in a physiologically acceptable carrier.

9. A pharmaceutical composition comprising at least one peptide according to claim 4 in a physiologically acceptable carrier.

10. A pharmaceutical composition comprising at least one peptide according to claim 5 in a physiologically acceptable carrier.

11. A lanthionine-bridged peptide of the formula:

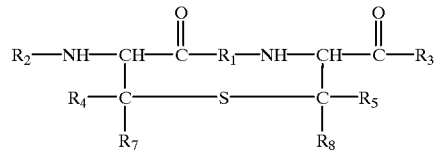

wherein $R_1$ represents Gly-Phe;

$R_2$ represents an amino acid selected from the group consisting of Phe, β-Nal, Tyr; or represents H, acyl or aracyl with 2 to 12 carbon atoms;

$R_3$ represents an amino acid selected from the group consisting of Phe, β-Nal, Tyr, TrpNH$_2$, Thr, ThrNH$_2$, Thr(ol), Ala and Ser; or represents OH or NH$_2$; or represents an amino acid sequence selected from the group consisting of Pro-Arg-Gly and Pro-Leu-Gly; or

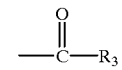

can be replaced by CH$_2$OH; and $R_4$, $R_5$, $R_7$ and $R_8$ independently represent hydrogen or a methyl group.

12. A pharmaceutical composition comprising at least one peptide according to claim 11 in a physiologically acceptable carrier.

* * * * *

```
                         SEQUENCE LISTING (1) GENERAL INFORMATION:

(iii) NUMBER OF SEQUENCES:   24

(2) INFORMATION FOR SEQ ID NO: 1:

(i) SEQUENCE CHARACTERISTICS:
         (A) LENGTH:   5
         (B) TYPE:   AMINO ACID
         (C) TOPOLOGY:   LINEAR (ii) MOLECULE TYPE:
         (A) DESCRIPTION:   PEPTIDE (iii) HYPOTHETICAL:   N/A (iv) ANTI-SENSE:   N/A (v) FRAGMENT TYPE:   INTERNAL (vi) ORIGINAL SOURCE:   AMINO ACIDS LISTED IN SEQUENCE -
             COMMERCIALLY AVAILABLE FROM BECHAN BIOSCIENCE,
             INC.,
             3700 MARKET STREET, PHILADELPHIA, PA   19104

(vii) IMMEDIATE SOURCE:   SYNTHESIZED PEPTIDE (viii) POSITION IN GENOME:   N/A (ix) FEATURE:
         (A) NAME/KEY:   ENANTIOMER
         (B) LOCATION:   -2
         (C) IDENTIFICATION METHOD:   amino acid analysis
             and
             mass spectrometry
         (D) OTHER INFORMATION:   water is removed and
             thereby
             a -S- bridge is present between Cys and Ser (x) PUBLICATION INFORMATION:
         (A) AUTHORS:   JUNG, GUNTHER
         (B) TITLE:   PEPTIDES WITH SULFIDE BRIDGES AND
             DEHYDROAMINO ACIDS:   THEIR PREPROPEPTIDES AND
             POSSIBILITIES FOR BIOENGINEERING
         (C) JOURNAL:   PROCEEDINGS OF THE 11TH AMERICAN
             PEPTIDE
             SYMPOSIUM
         (D) VOLUME:   ESCOM (LEIDEN 1990)
```

```
            (E) ISSUE:
            (F) PAGES:  865 - 869
            (G) DATE:   1990
            (H) DOCUMENT NUMBER:
            (I) FILING DATE:
            (J) PUBLICATION DATE:
            (K) RELEVANT RESIDUES IN SEQ ID NO: 1:  CYS-SER
                LANTHIONINE BRIDGE (xi) PUBLICATION INFORMATION:
            (A) AUTHORS:  SHIBA, TETSUO
                WAKAMIYA, TATEAKI
                FUKASE, KOICHI
                SANO, AKIHIKO
                SHIMBO, KUNIAKI
                UEKI, YASMYUKI
            (B) TITLE:  CHEMISTRY OF LANTHIONINE PEPTIDES
            (C) JOURNAL:  BIOPOLYMERS
            (D) VOLUME:  JOHN WILEY AND SONS, INC.
            (E) ISSUE:  SUPPLEMENTARY
            (F) PAGES:  511 - 519
            (G) DATE:   1986
            (H) DOCUMENT NUMBER:
            (I) FILING DATE:
            (J) PUBLICATION DATE:
            (K) RELEVANT RESIDUES IN SEQ ID NO: 1:  CYS-SER
                LANTHIONINE BRIDGE (xii) PUBLICATION INFORMATION:
            (A) AUTHORS:  BEAN, MARK F.
                CARR, STEVEN A.
                ESCHER, EMANUEL
                NEUGEBAUER, W.
                SAMANEN, JAMES
            (B) TITLE:  IDENTIFICATION OF A THIOETHER
                BY-PRODUCT
                IN THE SYNTHESIS OF A CYCLIC DISULFIDE PEPTIDE
                BY
                TANDEM MASS SPECTROMETRY
            (C) JOURNAL:  PROCEEDINGS OF THE 11TH AMERICAN
                PEPTIDE
                SYMPOSIUM
            (D) VOLUME:  ESCOM (LEIDEN 1990)
            (E) ISSUE:
            (F) PAGES:  443 - 445
            (G) DATE:   1990
            (H) DOCUMENT NUMBER:
            (I) FILING DATE:
            (J) PUBLICATION DATE:
            (K) RELEVANT RESIDUES IN SEQ ID NO: 1:  CYS-SER
                LANTHIONINE BRIDGE (xiii) SEQUENCE DESCRIPTION:  SEQ ID NO: 1:

Tyr Cys Gly Phe Ser
1             5

(2) INFORMATION FOR SEQ ID NO: 2:

(i) SEQUENCE CHARACTERISTICS:
            (A) LENGTH:  8
            (B) TYPE:  AMINO ACID
            (C) TOPOLOGY:  LINEAR (ii) MOLECULE TYPE:
            (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
                COMMERCIALLY AVAILABLE FROM BECHAN BIOSCIENCE,
                INC.,
                3700 MARKET STREET, PHILADELPHIA, PA  19104
```

```
     (vii) IMMEDIATE SOURCE: SYNTHESIZED PEPTIDE (viii) POSITION IN GENOME: N/A (ix) FEATURE:
           (A) NAME/KEY: ENANTIOMER
           (B) LOCATION: -4
           (C) IDENTIFICATION METHOD: amino acid analysis
                and
                mass spectrometry
           (D) OTHER INFORMATION: water is removed and
                thereby
                a -S- bridge is present between Cys and Ser (x) PUBLICATION INFORMATION:
           (A) AUTHORS: JUNG, GUNTHER
           (B) TITLE: PEPTIDES WITH SULFIDE BRIDGES AND
                DEHYDROAMINO ACIDS: THEIR PREPROPEPTIDES AND
                POSSIBILITIES FOR BIOENGINEERING
           (C) JOURNAL: PROCEEDINGS OF THE 11TH AMERICAN
                PEPTIDE
                SYMPOSIUM
           (D) VOLUME: ESCOM (LEIDEN 1990)
           (E) ISSUE:
           (F) PAGES: 865 - 869
           (G) DATE: 1990
           (H) DOCUMENT NUMBER:
           (I) FILING DATE:
           (J) PUBLICATION DATE:
           (K) RELEVANT RESIDUES IN SEQ ID NO: 2: CYS-SER
                LANTHIONINE BRIDGE (xi) PUBLICATION INFORMATION:
           (A) AUTHORS: SHIBA, TETSUO
                WAKAMIYA, TATEAKI
                FUKASE, KOICHI
                SANO, AKIHIKO
                SHIMBO, KUNIAKI
                UEKI, YASMYUKI
           (B) TITLE: CHEMISTRY OF LANTHIONINE PEPTIDES
           (C) JOURNAL: BIOPOLYMERS
           (D) VOLUME: JOHN WILEY AND SONS, INC.
           (E) ISSUE: SUPPLEMENTARY
           (F) PAGES: 511 - 519
           (G) DATE: 1986
           (H) DOCUMENT NUMBER:
           (I) FILING DATE:
           (J) PUBLICATION DATE:
           (K) RELEVANT RESIDUES IN SEQ ID NO: 2: CYS-SER
                LANTHIONINE BRIDGE (xii) PUBLICATION INFORMATION:
           (A) AUTHORS: BEAN, MARK F.
                CARR, STEVEN A.
                ESCHER, EMANUEL
                NEUGEBAUER, W.
                SAMANEN, JAMES
           (B) TITLE: IDENTIFICATION OF A THIOETHER
                BY-PRODUCT
                IN THE SYNTHESIS OF A CYCLIC DISULFIDE PEPTIDE
                BY
                TANDEM MASS SPECTROMETRY
           (C) JOURNAL: PROCEEDINGS OF THE 11TH AMERICAN
                PEPTIDE
                SYMPOSIUM
           (D) VOLUME: ESCOM (LEIDEN 1990)
           (E) ISSUE:
           (F) PAGES: 443 - 445
           (G) DATE: 1990
           (H) DOCUMENT NUMBER:
           (I) FILING DATE:
           (J) PUBLICATION DATE:
           (K) RELEVANT RESIDUES IN SEQ ID NO: 2: CYS-SER
                LANTHIONINE BRIDGE (xiii) SEQUENCE DESCRIPTION: SEQ ID NO: 2:

Phe Cys Phe Trp Lys Thr Ser Thr
1               5
```

```
(2) INFORMATION FOR SEQ ID NO: 3:

(i) SEQUENCE CHARACTERISTICS:
        (A) LENGTH:  8
        (B) TYPE:  AMINO ACID
        (C) TOPOLOGY:  LINEAR (ii) MOLECULE TYPE:
        (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
             COMMERCIALLY AVAILABLE FROM BECHAN BIOSCIENCE,
             INC.,
             3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
        (A) NAME/KEY:  ENANTIOMER
        (B) LOCATION:  -4
        (C) IDENTIFICATION METHOD:  amino acid analysis
            and
            mass spectrometry
        (D) OTHER INFORMATION:  water is removed and
            thereby
            a -S- bridge is present between Cys and Ser (x) PUBLICATION INFORMATION:
        (A) AUTHORS:  JUNG, GUNTHER
        (B) TITLE:  PEPTIDES WITH SULFIDE BRIDGES AND
            DEHYDROAMINO ACIDS:  THEIR PREPROPEPTIDES AND
            POSSIBILITIES FOR BIOENGINEERING
        (C) JOURNAL:  PROCEEDINGS OF THE 11TH AMERICAN
            PEPTIDE
            SYMPOSIUM
        (D) VOLUME:  ESCOM (LEIDEN 1990)
        (E) ISSUE:
        (F) PAGES:  865 - 869
        (G) DATE:  1990
        (H) DOCUMENT NUMBER:
        (I) FILING DATE:
        (J) PUBLICATION DATE:
        (K) RELEVANT RESIDUES IN SEQ ID NO: 3:  CYS-SER
            LANTHIONINE BRIDGE (xi) PUBLICATION INFORMATION:
        (A) AUTHORS:  SHIBA, TETSUO
            WAKAMIYA, TATEAKI
            FUKASE, KOICHI
            SANO, AKIHIKO
            SHIMBO, KUNIAKI
            UEKI, YASMYUKI
        (B) TITLE:  CHEMISTRY OF LANTHIONINE PEPTIDES
        (C) JOURNAL:  BIOPOLYMERS
        (D) VOLUME:  JOHN WILEY AND SONS, INC.
        (E) ISSUE:  SUPPLEMENTARY
        (F) PAGES:  511 - 519
        (G) DATE:  1986
        (H) DOCUMENT NUMBER:
        (I) FILING DATE:
        (J) PUBLICATION DATE:
        (K) RELEVANT RESIDUES IN SEQ ID NO: 3:  CYS-SER
            LANTHIONINE BRIDGE (xii) PUBLICATION INFORMATION:
        (A) AUTHORS:  BEAN, MARK F.
            CARR, STEVEN A.
            ESCHER, EMANUEL
            NEUGEBAUER, W.
```

```
                SAMANEN, JAMES
        (B) TITLE:  IDENTIFICATION OF A THIOETHER
            BY-PRODUCT
            IN THE SYNTHESIS OF A CYCLIC DISULFIDE PEPTIDE
            BY
            TANDEM MASS SPECTROMETRY
        (C) JOURNAL:  PROCEEDINGS OF THE 11TH AMERICAN
            PEPTIDE
            SYMPOSIUM
        (D) VOLUME:  ESCOM (LEIDEN 1990)
        (E) ISSUE:
        (F) PAGES:  443 - 445
        (G) DATE:  1990
        (H) DOCUMENT NUMBER:
        (I) FILING DATE:
        (J) PUBLICATION DATE:
        (K) RELEVANT RESIDUES IN SEQ ID NO: 3:  CYS-SER
            LANTHIONINE BRIDGE AND GENERAL PEPTIDE
            STRUCTURE (xiii) SEQUENCE DESCRIPTION:  SEQ ID NO: 3:

Xaa Cys Phe Trp Lys Thr Ser Thr
1               5

(2) INFORMATION FOR SEQ ID NO: 4:

(i) SEQUENCE CHARACTERISTICS:
        (A) LENGTH:  8
        (B) TYPE:  AMINO ACID
        (C) TOPOLOGY:  LINEAR (ii) MOLECULE TYPE:
        (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
            COMMERCIALLY AVAILABLE FROM BECHAN BIOSCIENCE,
            INC.,
            3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
        (A) NAME/KEY:  ENANTIOMER
        (B) LOCATION:  -4
        (C) IDENTIFICATION METHOD:  amino acid analysis
            and
            mass spectrometry
        (D) OTHER INFORMATION:  water is removed and
            thereby
            a -S- bridge is present between Cys and Ser (x) PUBLICATION INFORMATION:
        (A) AUTHORS:  JUNG, GUNTHER
        (B) TITLE:  PEPTIDES WITH SULFIDE BRIDGES AND
            DEHYDROAMINO ACIDS:  THEIR PREPROPEPTIDES AND
            POSSIBILITIES FOR BIOENGINEERING
        (C) JOURNAL:  PROCEEDINGS OF THE 11TH AMERICAN
            PEPTIDE
            SYMPOSIUM
        (D) VOLUME:  ESCOM (LEIDEN 1990)
        (E) ISSUE:
        (F) PAGES:  865 - 869
        (G) DATE:  1990
        (H) DOCUMENT NUMBER:
        (I) FILING DATE:
        (J) PUBLICATION DATE:
        (K) RELEVANT RESIDUES IN SEQ ID NO: 4:  CYS-SER
            LANTHIONINE BRIDGE
```

```
    (xi) PUBLICATION INFORMATION:
         (A) AUTHORS:  SHIBA, TETSUO
              WAKAMIYA, TATEAKI
              FUKASE, KOICHI
              SANO, AKIHIKO
              SHIMBO, KUNIAKI
              UEKI, YASMYUKI
         (B) TITLE:  CHEMISTRY OF LANTHIONINE PEPTIDES
         (C) JOURNAL:  BIOPOLYMERS
         (D) VOLUME:  JOHN WILEY AND SONS, INC.
         (E) ISSUE:  SUPPLEMENTARY
         (F) PAGES:  511 - 519
         (G) DATE:  1986
         (H) DOCUMENT NUMBER:
         (I) FILING DATE:
         (J) PUBLICATION DATE:
         (K) RELEVANT RESIDUES IN SEQ ID NO: 4:  CYS-SER
             LANTHIONINE BRIDGE (xii) PUBLICATION INFORMATION:
         (A) AUTHORS:  BEAN, MARK F.
              CARR, STEVEN A.
              ESCHER, EMANUEL
              NEUGEBAUER, W.
              SAMANEN, JAMES
         (B) TITLE:  IDENTIFICATION OF A THIOETHER
             BY-PRODUCT
             IN THE SYNTHESIS OF A CYCLIC DISULFIDE PEPTIDE
             BY
             TANDEM MASS SPECTROMETRY
         (C) JOURNAL:  PROCEEDINGS OF THE 11TH AMERICAN
             PEPTIDE
             SYMPOSIUM
         (D) VOLUME:  ESCOM (LEIDEN 1990)
         (E) ISSUE:
         (F) PAGES:  443 - 445
         (G) DATE:  1990
         (H) DOCUMENT NUMBER:
         (I) FILING DATE:
         (J) PUBLICATION DATE:
         (K) RELEVANT RESIDUES IN SEQ ID NO: 4:  CYS-SER
             LANTHIONINE BRIDGE AND GENERAL PEPTIDE
             STRUCTURE (xiii) SEQUENCE DESCRIPTION:  SEQ ID NO: 4:

Xaa Cys Phe Trp Lys Thr Ser Thr
1               5

(2) INFORMATION FOR SEQ ID NO: 5:

(i) SEQUENCE CHARACTERISTICS:
         (A) LENGTH:  8
         (B) TYPE:  AMINO ACID
         (C) TOPOLOGY:  LINEAR (ii) MOLECULE TYPE:
         (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
              COMMERCIALLY AVAILABLE FROM BECHAN BIOSCIENCE,
              INC.,
              3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
         (A) NAME/KEY:  ENANTIOMER
         (B) LOCATION:  -4
         (C) IDENTIFICATION METHOD:  amino acid analysis
```

```
                    and
                    mass spectrometry
          (D) OTHER INFORMATION:  water is removed and
                    thereby
                    a -S- bridge is present between Cys and Ser (x) PUBLICATION INFORMATION:
         (A) AUTHORS:  JUNG, GUNTHER
         (B) TITLE:  PEPTIDES WITH SULFIDE BRIDGES AND
                DEHYDROAMINO ACIDS:  THEIR PREPROPEPTIDES AND
                POSSIBILITIES FOR BIOENGINEERING
         (C) JOURNAL:  PROCEEDINGS OF THE 11TH AMERICAN
                PEPTIDE
                SYMPOSIUM
         (D) VOLUME:  ESCOM (LEIDEN 1990)
         (E) ISSUE:
         (F) PAGES:  865 - 869
         (G) DATE:  1990
         (H) DOCUMENT NUMBER:
         (I) FILING DATE:
         (J) PUBLICATION DATE:
         (K) RELEVANT RESIDUES IN SEQ ID NO: 5:  CYS-SER
                LANTHIONINE BRIDGE (xi) PUBLICATION INFORMATION:
         (A) AUTHORS:  SHIBA, TETSUO
                WAKAMIYA, TATEAKI
                FUKASE, KOICHI
                SANO, AKIHIKO
                SHIMBO, KUNIAKI
                UEKI, YASMYUKI
         (B) TITLE:  CHEMISTRY OF LANTHIONINE PEPTIDES
         (C) JOURNAL:  BIOPOLYMERS
         (D) VOLUME:  JOHN WILEY AND SONS, INC.
         (E) ISSUE:  SUPPLEMENTARY
         (F) PAGES:  511 - 519
         (G) DATE:  1986
         (H) DOCUMENT NUMBER:
         (I) FILING DATE:
         (J) PUBLICATION DATE:
         (K) RELEVANT RESIDUES IN SEQ ID NO: 5:  CYS-SER
                LANTHIONINE BRIDGE (xii) PUBLICATION INFORMATION:
         (A) AUTHORS:  BEAN, MARK F.
                CARR, STEVEN A.
                ESCHER, EMANUEL
                NEUGEBAUER, W.
                SAMANEN, JAMES
         (B) TITLE:  IDENTIFICATION OF A THIOETHER
                BY-PRODUCT
                IN THE SYNTHESIS OF A CYCLIC DISULFIDE PEPTIDE
                BY
                TANDEM MASS SPECTROMETRY
         (C) JOURNAL:  PROCEEDINGS OF THE 11TH AMERICAN
                PEPTIDE
                SYMPOSIUM
         (D) VOLUME:  ESCOM (LEIDEN 1990)
         (E) ISSUE:
         (F) PAGES:  443 - 445
         (G) DATE:  1990
         (H) DOCUMENT NUMBER:
         (I) FILING DATE:
         (J) PUBLICATION DATE:
         (K) RELEVANT RESIDUES IN SEQ ID NO: 5:  CYS-SER
                LANTHIONINE BRIDGE AND GENERAL PEPTIDE
                STRUCTURE (xiii) SEQUENCE DESCRIPTION:  SEQ ID NO: 5:

Phe Cys Phe Trp Lys Thr Ser Trp
1               5

(2) INFORMATION FOR SEQ ID NO: 6:

(i) SEQUENCE CHARACTERISTICS:
         (A) LENGTH:  8
         (B) TYPE:  AMINO ACID
```

```
            (C) TOPOLOGY:  LINEAR (ii) MOLECULE TYPE:
       (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
            COMMERCIALLY AVAILABLE FROM BECHAN BIOSCIENCE,
            INC.,
            3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
       (A) NAME/KEY:  ENANTIOMER
       (B) LOCATION:  -4
       (C) IDENTIFICATION METHOD:  amino acid analysis
            and
            mass spectrometry
       (D) OTHER INFORMATION:  water is removed and
            thereby
            a -S- bridge is present between Cys and Ser (x) PUBLICATION INFORMATION:
       (A) AUTHORS:  JUNG, GUNTHER
       (B) TITLE:  PEPTIDES WITH SULFIDE BRIDGES AND
            DEHYDROAMINO ACIDS:  THEIR PREPROPEPTIDES AND
            POSSIBILITIES FOR BIOENGINEERING
       (C) JOURNAL:  PROCEEDINGS OF THE 11TH AMERICAN
            PEPTIDE
            SYMPOSIUM
       (D) VOLUME:  ESCOM (LEIDEN 1990)
       (E) ISSUE:
       (F) PAGES:  865 - 869
       (G) DATE:  1990
       (H) DOCUMENT NUMBER:
       (I) FILING DATE:
       (J) PUBLICATION DATE:
       (K) RELEVANT RESIDUES IN SEQ ID NO: 6:  CYS-SER
            LANTHIONINE BRIDGE (xi) PUBLICATION INFORMATION:
       (A) AUTHORS:  SHIBA, TETSUO
            WAKAMIYA, TATEAKI
            FUKASE, KOICHI
            SANO, AKIHIKO
            SHIMBO, KUNIAKI
            UEKI, YASMYUKI
       (B) TITLE:  CHEMISTRY OF LANTHIONINE PEPTIDES
       (C) JOURNAL:  BIOPOLYMERS
       (D) VOLUME:  JOHN WILEY AND SONS, INC.
       (E) ISSUE:  SUPPLEMENTARY
       (F) PAGES:  511 - 519
       (G) DATE:  1986
       (H) DOCUMENT NUMBER:
       (I) FILING DATE:
       (J) PUBLICATION DATE:
       (K) RELEVANT RESIDUES IN SEQ ID NO: 6:  CYS-SER
            LANTHIONINE BRIDGE (xii) PUBLICATION INFORMATION:
       (A) AUTHORS:  BEAN, MARK F.
            CARR, STEVEN A.
            ESCHER, EMANUEL
            NEUGEBAUER, W.
            SAMANEN, JAMES
       (B) TITLE:  IDENTIFICATION OF A THIOETHER
            BY-PRODUCT
            IN THE SYNTHESIS OF A CYCLIC DISULFIDE PEPTIDE
            BY
            TANDEM MASS SPECTROMETRY
       (C) JOURNAL:  PROCEEDINGS OF THE 11TH AMERICAN
```

```
                    PEPTIDE
                    SYMPOSIUM
            (D) VOLUME:  ESCOM (LEIDEN 1990)
            (E) ISSUE:
            (F) PAGES:  443 - 445
            (G) DATE:  1990
            (H) DOCUMENT NUMBER:
            (I) FILING DATE:
            (J) PUBLICATION DATE:
            (K) RELEVANT RESIDUES IN SEQ ID NO: 6:  CYS-SER
                LANTHIONINE BRIDGE AND GENERAL PEPTIDE
                STRUCTURE (xiii) SEQUENCE DESCRIPTION:  SEQ ID NO: 6:

Xaa Cys Phe Trp Lys Thr Ser Trp
1               5

(2) INFORMATION FOR SEQ ID NO: 7:

(i) SEQUENCE CHARACTERISTICS:
           (A) LENGTH:  8
           (B) TYPE:  AMINO ACID
           (C) TOPOLOGY:  LINEAR (ii) MOLECULE TYPE:
           (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
                COMMERCIALLY AVAILABLE FROM BECHAN BIOSCIENCE,
                INC.,
                3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
           (A) NAME/KEY:  ENANTIOMER
           (B) LOCATION:  -4
           (C) IDENTIFICATION METHOD:  amino acid analysis
               and
               mass spectrometry
           (D) OTHER INFORMATION:  water is removed and
               thereby
               a -S- bridge is present between Cys and Ser (x) PUBLICATION INFORMATION:
           (A) AUTHORS:  JUNG, GUNTHER
           (B) TITLE:  PEPTIDES WITH SULFIDE BRIDGES AND
               DEHYDROAMINO ACIDS:  THEIR PREPROPEPTIDES AND
               POSSIBILITIES FOR BIOENGINEERING
           (C) JOURNAL:  PROCEEDINGS OF THE 11TH AMERICAN
               PEPTIDE
               SYMPOSIUM
           (D) VOLUME:  ESCOM (LEIDEN 1990)
           (E) ISSUE:
           (F) PAGES:  865 - 869
           (G) DATE:  1990
           (H) DOCUMENT NUMBER:
           (I) FILING DATE:
           (J) PUBLICATION DATE:
           (K) RELEVANT RESIDUES IN SEQ ID NO: 7:  CYS-SER
               LANTHIONINE BRIDGE (xi) PUBLICATION INFORMATION:
           (A) AUTHORS:  SHIBA, TETSUO
               WAKAMIYA, TATEAKI
               FUKASE, KOICHI
               SANO, AKIHIKO
               SHIMBO, KUNIAKI
               UEKI, YASMYUKI
```

```
            (B) TITLE:  CHEMISTRY OF LANTHIONINE PEPTIDES
            (C) JOURNAL:  BIOPOLYMERS
            (D) VOLUME:  JOHN WILEY AND SONS, INC.
            (E) ISSUE:  SUPPLEMENTARY
            (F) PAGES:  511 - 519
            (G) DATE:  1986
            (H) DOCUMENT NUMBER:
            (I) FILING DATE:
            (J) PUBLICATION DATE:
            (K) RELEVANT RESIDUES IN SEQ ID NO: 7:  CYS-SER
                LANTHIONINE BRIDGE (xii) PUBLICATION INFORMATION:
            (A) AUTHORS:  BEAN, MARK F.
                  CARR, STEVEN A.
                  ESCHER, EMANUEL
                  NEUGEBAUER, W.
                  SAMANEN, JAMES
            (B) TITLE:  IDENTIFICATION OF A THIOETHER
                BY-PRODUCT
                IN THE SYNTHESIS OF A CYCLIC DISULFIDE PEPTIDE
                BY
                TANDEM MASS SPECTROMETRY
            (C) JOURNAL:  PROCEEDINGS OF THE 11TH AMERICAN
                PEPTIDE
                SYMPOSIUM
            (D) VOLUME:  ESCOM (LEIDEN 1990)
            (E) ISSUE:
            (F) PAGES:  443 - 445
            (G) DATE:  1990
            (H) DOCUMENT NUMBER:
            (I) FILING DATE:
            (J) PUBLICATION DATE:
            (K) RELEVANT RESIDUES IN SEQ ID NO: 7:  CYS-SER
                LANTHIONINE BRIDGE AND GENERAL PEPTIDE
                STRUCTURE (xiii) SEQUENCE DESCRIPTION:  SEQ ID NO: 7:

Phe Cys Phe Trp Lys Val Ser Trp
1               5

(2) INFORMATION FOR SEQ ID NO: 8:

(i) SEQUENCE CHARACTERISTICS:
            (A) LENGTH:  8
            (B) TYPE:  AMINO ACID
            (C) TOPOLOGY:  LINEAR (ii) MOLECULE TYPE:
            (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
                 COMMERCIALLY AVAILABLE FROM BECHAN BIOSCIENCE,
                 INC.,
                 3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
            (A) NAME/KEY:  ENANTIOMER
            (B) LOCATION:  -4
            (C) IDENTIFICATION METHOD:  amino acid analysis
                and
                mass spectrometry
            (D) OTHER INFORMATION:  water is removed and
                thereby
                a -S- bridge is present between Cys and Ser (x) PUBLICATION INFORMATION:
```

```
            (A) AUTHORS:  JUNG, GUNTHER
            (B) TITLE:  PEPTIDES WITH SULFIDE BRIDGES AND
                DEHYDROAMINO ACIDS:  THEIR PREPROPEPTIDES AND
                POSSIBILITIES FOR BIOENGINEERING
            (C) JOURNAL:  PROCEEDINGS OF THE 11TH AMERICAN
                PEPTIDE
                SYMPOSIUM
            (D) VOLUME:  ESCOM (LEIDEN 1990)
            (E) ISSUE:
            (F) PAGES:  865 - 869
            (G) DATE:  1990
            (H) DOCUMENT NUMBER:
            (I) FILING DATE:
            (J) PUBLICATION DATE:
            (K) RELEVANT RESIDUES IN SEQ ID NO: 8:  CYS-SER
                LANTHIONINE BRIDGE (xi) PUBLICATION INFORMATION:
            (A) AUTHORS:  SHIBA, TETSUO
                WAKAMIYA, TATEAKI
                FUKASE, KOICHI
                SANO, AKIHIKO
                SHIMBO, KUNIAKI
                UEKI, YASMYUKI
            (B) TITLE:  CHEMISTRY OF LANTHIONINE PEPTIDES
            (C) JOURNAL:  BIOPOLYMERS
            (D) VOLUME:  JOHN WILEY AND SONS, INC.
            (E) ISSUE:  SUPPLEMENTARY
            (F) PAGES:  511 - 519
            (G) DATE:  1986
            (H) DOCUMENT NUMBER:
            (I) FILING DATE:
            (J) PUBLICATION DATE:
            (K) RELEVANT RESIDUES IN SEQ ID NO: 8:  CYS-SER
                LANTHIONINE BRIDGE (xii) PUBLICATION INFORMATION:
            (A) AUTHORS:  BEAN, MARK F.
                CARR, STEVEN A.
                ESCHER, EMANUEL
                NEUGEBAUER, W.
                SAMANEN, JAMES
            (B) TITLE:  IDENTIFICATION OF A THIOETHER
                BY-PRODUCT
                IN THE SYNTHESIS OF A CYCLIC DISULFIDE PEPTIDE
                BY
                TANDEM MASS SPECTROMETRY
            (C) JOURNAL:  PROCEEDINGS OF THE 11TH AMERICAN
                PEPTIDE
                SYMPOSIUM
            (D) VOLUME:  ESCOM (LEIDEN 1990)
            (E) ISSUE:
            (F) PAGES:  443 - 445
            (G) DATE:  1990
            (H) DOCUMENT NUMBER:
            (I) FILING DATE:
            (J) PUBLICATION DATE:
            (K) RELEVANT RESIDUES IN SEQ ID NO: 8:  CYS-SER
                LANTHIONINE BRIDGE  AND GENERAL PEPTIDE
                STRUCTURE (xiii) SEQUENCE DESCRIPTION:  SEQ ID NO: 8:

Xaa Cys Phe Trp Lys Val Ser Trp
1               5

(2) INFORMATION FOR SEQ ID NO: 9:

(i) SEQUENCE CHARACTERISTICS:
            (A) LENGTH:  8
            (B) TYPE:  AMINO ACID
            (C) TOPOLOGY:  LINEAR (ii) MOLECULE TYPE:
            (A) DESCRIPTION:  PEPTIDE (iii) HYPOTHETICAL:  N/A
```

```
  (iv) ANTI-SENSE: N/A (v) FRAGMENT TYPE: INTERNAL (vi) ORIGINAL SOURCE: AMINO ACIDS LISTED IN SEQUENCE -
            COMMERCIALLY AVAILABLE FROM BECHAN BIOSCIENCE,
            INC.,
            3700 MARKET STREET, PHILADELPHIA, PA  19104

(vii) IMMEDIATE SOURCE: SYNTHESIZED PEPTIDE (viii) POSITION IN GENOME: N/A (ix) FEATURE:
            (A) NAME/KEY: ENANTIOMER
            (B) LOCATION: -4
            (C) IDENTIFICATION METHOD:  amino acid analysis
                and
                mass spectrometry
            (D) OTHER INFORMATION:  water is removed and
                thereby
                a -S- bridge is present between Cys and Ser (x) PUBLICATION INFORMATION:
            (A) AUTHORS: JUNG, GUNTHER
            (B) TITLE: PEPTIDES WITH SULFIDE BRIDGES AND
                DEHYDROAMINO ACIDS:  THEIR PREPROPEPTIDES AND
                POSSIBILITIES FOR BIOENGINEERING
            (C) JOURNAL: PROCEEDINGS OF THE 11TH AMERICAN
                PEPTIDE
                SYMPOSIUM
            (D) VOLUME: ESCOM (LEIDEN 1990)
            (E) ISSUE:
            (F) PAGES: 865 - 869
            (G) DATE: 1990
            (H) DOCUMENT NUMBER:
            (I) FILING DATE:
            (J) PUBLICATION DATE:
            (K) RELEVANT RESIDUES IN SEQ ID NO: 9:  CYS-SER
                LANTHIONINE BRIDGE (xi) PUBLICATION INFORMATION:
            (A) AUTHORS: SHIBA, TETSUO
                WAKAMIYA, TATEAKI
                FUKASE, KOICHI
                SANO, AKIHIKO
                SHIMBO, KUNIAKI
                UEKI, YASMYUKI
            (B) TITLE: CHEMISTRY OF LANTHIONINE PEPTIDES
            (C) JOURNAL: BIOPOLYMERS
            (D) VOLUME: JOHN WILEY AND SONS, INC.
            (E) ISSUE: SUPPLEMENTARY
            (F) PAGES: 511 - 519
            (G) DATE: 1986
            (H) DOCUMENT NUMBER:
            (I) FILING DATE:
            (J) PUBLICATION DATE:
            (K) RELEVANT RESIDUES IN SEQ ID NO: 9:  CYS-SER
                LANTHIONINE BRIDGE (xii) PUBLICATION INFORMATION:
            (A) AUTHORS: BEAN, MARK F.
                CARR, STEVEN A.
                ESCHER, EMANUEL
                NEUGEBAUER, W.
                SAMANEN, JAMES
            (B) TITLE: IDENTIFICATION OF A THIOETHER
                BY-PRODUCT
                IN THE SYNTHESIS OF A CYCLIC DISULFIDE PEPTIDE
                BY
                TANDEM MASS SPECTROMETRY
            (C) JOURNAL: PROCEEDINGS OF THE 11TH AMERICAN
                PEPTIDE
                SYMPOSIUM
            (D) VOLUME: ESCOM (LEIDEN 1990)
            (E) ISSUE:
            (F) PAGES: 443 - 445
            (G) DATE: 1990
            (H) DOCUMENT NUMBER:
```

```
            (I) FILING DATE:
            (J) PUBLICATION DATE:
            (K) RELEVANT RESIDUES IN SEQ ID NO: 9:  CYS-SER
                LANTHIONINE BRIDGE AND GENERAL PEPTIDE
                STRUCTURE (xiii) SEQUENCE DESCRIPTION:  SEQ ID NO: 9:

Phe Cys Phe Trp Lys Val Ser Thr
1               5

(2) INFORMATION FOR SEQ ID NO: 10:

(i) SEQUENCE CHARACTERISTICS:
            (A) LENGTH:  8
            (B) TYPE:  AMINO ACID
            (C) TOPOLOGY:  LINEAR (ii) MOLECULE TYPE:
            (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
                COMMERCIALLY AVAILABLE FROM BECHAN BIOSCIENCE,
                INC.,
                3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
            (A) NAME/KEY:  ENANTIOMER
            (B) LOCATION:  -4
            (C) IDENTIFICATION METHOD:  amino acid analysis
                and
                mass spectrometry
            (D) OTHER INFORMATION:  water is removed and
                thereby
                a -S- bridge is present between Cys and Ser (x) PUBLICATION INFORMATION:
            (A) AUTHORS:  JUNG, GUNTHER
            (B) TITLE:  PEPTIDES WITH SULFIDE BRIDGES AND
                DEHYDROAMINO ACIDS:  THEIR PREPROPEPTIDES AND
                POSSIBILITIES FOR BIOENGINEERING
            (C) JOURNAL:  PROCEEDINGS OF THE 11TH AMERICAN
                PEPTIDE
                SYMPOSIUM
            (D) VOLUME:  ESCOM (LEIDEN 1990)
            (E) ISSUE:
            (F) PAGES:  865 - 869
            (G) DATE:  1990
            (H) DOCUMENT NUMBER:
            (I) FILING DATE:
            (J) PUBLICATION DATE:
            (K) RELEVANT RESIDUES IN SEQ ID NO: 10:  CYS-SER
                LANTHIONINE BRIDGE (xi) PUBLICATION INFORMATION:
            (A) AUTHORS:  SHIBA, TETSUO
                WAKAMIYA, TATEAKI
                FUKASE, KOICHI
                SANO, AKIHIKO
                SHIMBO, KUNIAKI
                UEKI, YASMYUKI
            (B) TITLE:  CHEMISTRY OF LANTHIONINE PEPTIDES
            (C) JOURNAL:  BIOPOLYMERS
            (D) VOLUME:  JOHN WILEY AND SONS, INC.
            (E) ISSUE:  SUPPLEMENTARY
            (F) PAGES:  511 - 519
            (G) DATE:  1986
            (H) DOCUMENT NUMBER:
```

```
            (I) FILING DATE:
            (J) PUBLICATION DATE:
            (K) RELEVANT RESIDUES IN SEQ ID NO: 10:  CYS-SER
                LANTHIONINE BRIDGE (xii) PUBLICATION INFORMATION:
            (A) AUTHORS:  BEAN, MARK F.
                CARR, STEVEN A.
                ESCHER, EMANUEL
                NEUGEBAUER, W.
                SAMANEN, JAMES
            (B) TITLE:  IDENTIFICATION OF A THIOETHER
                BY-PRODUCT
                IN THE SYNTHESIS OF A CYCLIC DISULFIDE PEPTIDE
                BY
                TANDEM MASS SPECTROMETRY
            (C) JOURNAL:  PROCEEDINGS OF THE 11TH AMERICAN
                PEPTIDE
                SYMPOSIUM
            (D) VOLUME:  ESCOM (LEIDEN 1990)
            (E) ISSUE:
            (F) PAGES:  443 - 445
            (G) DATE:  1990
            (H) DOCUMENT NUMBER:
            (I) FILING DATE:
            (J) PUBLICATION DATE:
            (K) RELEVANT RESIDUES IN SEQ ID NO: 10:  CYS-SER
                LANTHIONINE BRIDGE AND GENERAL PEPTIDE
                STRUCTURE (xiii) SEQUENCE DESCRIPTION:  SEQ ID NO: 10:

Xaa Cys Phe Trp Lys Val Ser Thr
1               5

(2) INFORMATION FOR SEQ ID NO: 11:

(i) SEQUENCE CHARACTERISTICS:
            (A) LENGTH:  8
            (B) TYPE:  AMINO ACID
            (C) TOPOLOGY:  LINEAR (ii) MOLECULE TYPE:
            (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
                COMMERCIALLY AVAILABLE FROM BECHAN BIOSCIENCE,
                INC.,
                3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
            (A) NAME/KEY:  ENANTIOMER
            (B) LOCATION:  -4
            (C) IDENTIFICATION METHOD:  amino acid analysis
                and
                mass spectrometry
            (D) OTHER INFORMATION:  water is removed and
                thereby
                a -S- bridge is present between Cys and Ser (x) PUBLICATION INFORMATION:
            (A) AUTHORS:  JUNG, GUNTHER
            (B) TITLE:  PEPTIDES WITH SULFIDE BRIDGES AND
                DEHYDROAMINO ACIDS:  THEIR PREPROPEPTIDES AND
                POSSIBILITIES FOR BIOENGINEERING
            (C) JOURNAL:  PROCEEDINGS OF THE 11TH AMERICAN
                PEPTIDE
                SYMPOSIUM
```

```
            (D) VOLUME:  ESCOM (LEIDEN 1990)
            (E) ISSUE:
            (F) PAGES:  865 - 869
            (G) DATE:  1990
            (H) DOCUMENT NUMBER:
            (I) FILING DATE:
            (J) PUBLICATION DATE:
            (K) RELEVANT RESIDUES IN SEQ ID NO: 11:  CYS-SER
                LANTHIONINE BRIDGE (xi) PUBLICATION INFORMATION:
            (A) AUTHORS:  SHIBA, TETSUO
                WAKAMIYA, TATEAKI
                FUKASE, KOICHI
                SANO, AKIHIKO
                SHIMBO, KUNIAKI
                UEKI, YASMYUKI
            (B) TITLE:  CHEMISTRY OF LANTHIONINE PEPTIDES
            (C) JOURNAL:  BIOPOLYMERS
            (D) VOLUME:  JOHN WILEY AND SONS, INC.
            (E) ISSUE:  SUPPLEMENTARY
            (F) PAGES:  511 - 519
            (G) DATE:  1986
            (H) DOCUMENT NUMBER:
            (I) FILING DATE:
            (J) PUBLICATION DATE:
            (K) RELEVANT RESIDUES IN SEQ ID NO: 11:  CYS-SER
                LANTHIONINE BRIDGE (xii) PUBLICATION INFORMATION:
            (A) AUTHORS:  BEAN, MARK F.
                CARR, STEVEN A.
                ESCHER, EMANUEL
                NEUGEBAUER, W.
                SAMANEN, JAMES
            (B) TITLE:  IDENTIFICATION OF A THIOETHER
                BY-PRODUCT
                IN THE SYNTHESIS OF A CYCLIC DISULFIDE PEPTIDE
                BY
                TANDEM MASS SPECTROMETRY
            (C) JOURNAL:  PROCEEDINGS OF THE 11TH AMERICAN
                PEPTIDE
                SYMPOSIUM
            (D) VOLUME:  ESCOM (LEIDEN 1990)
            (E) ISSUE:
            (F) PAGES:  443 - 445
            (G) DATE:  1990
            (H) DOCUMENT NUMBER:
            (I) FILING DATE:
            (J) PUBLICATION DATE:
            (K) RELEVANT RESIDUES IN SEQ ID NO: 11:  CYS-SER
                LANTHIONINE BRIDGE AND GENERAL PEPTIDE
                STRUCTURE (xiii) SEQUENCE DESCRIPTION:  SEQ ID NO: 11:

Xaa Cys Phe Trp Lys Val Ser Thr
1               5

(2) INFORMATION FOR SEQ ID NO: 12:

(i) SEQUENCE CHARACTERISTICS:
            (A) LENGTH:  9
            (B) TYPE:  AMINO ACID
            (C) TOPOLOGY:  LINEAR (ii) MOLECULE TYPE:
            (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
            COMMERCIALLY AVAILABLE FROM BECHAN BIOSCIENCE,
            INC.,
```

```
                    3700 MARKET STREET, PHILADELPHIA, PA   19104

(vii) IMMEDIATE SOURCE:   SYNTHESIZED PEPTIDE (viii) POSITION IN GENOME:   N/A (ix) FEATURE:
        (A) NAME/KEY:   N/A
        (B) LOCATION:   N/A
        (C) IDENTIFICATION METHOD:   N/A
        (D) OTHER INFORMATION:   water is removed and
             thereby
             a -S- bridge is present between Cys and Ser (x) PUBLICATION INFORMATION:
        (A) AUTHORS:   JUNG, GUNTHER
        (B) TITLE:   PEPTIDES WITH SULFIDE BRIDGES AND
             DEHYDROAMINO ACIDS:   THEIR PREPROPEPTIDES AND
             POSSIBILITIES FOR BIOENGINEERING
        (C) JOURNAL:   PROCEEDINGS OF THE 11TH AMERICAN
             PEPTIDE
             SYMPOSIUM
        (D) VOLUME:   ESCOM (LEIDEN 1990)
        (E) ISSUE:
        (F) PAGES:   865 - 869
        (G) DATE:   1990
        (H) DOCUMENT NUMBER:
        (I) FILING DATE:
        (J) PUBLICATION DATE:
        (K) RELEVANT RESIDUES IN SEQ ID NO: 12:   CYS-SER
             LANTHIONINE BRIDGE (xi) PUBLICATION INFORMATION:
        (A) AUTHORS:   SHIBA, TETSUO
               WAKAMIYA, TATEAKI
               FUKASE, KOICHI
               SANO, AKIHIKO
               SHIMBO, KUNIAKI
               UEKI, YASMYUKI
        (B) TITLE:   CHEMISTRY OF LANTHIONINE PEPTIDES
        (C) JOURNAL:   BIOPOLYMERS
        (D) VOLUME:   JOHN WILEY AND SONS, INC.
        (E) ISSUE:   SUPPLEMENTARY
        (F) PAGES:   511 - 519
        (G) DATE:   1986
        (H) DOCUMENT NUMBER:
        (I) FILING DATE:
        (J) PUBLICATION DATE:
        (K) RELEVANT RESIDUES IN SEQ ID NO: 12:   CYS-SER
             LANTHIONINE BRIDGE (xii) PUBLICATION INFORMATION:
        (A) AUTHORS:   BEAN, MARK F.
               CARR, STEVEN A.
               ESCHER, EMANUEL
               NEUGEBAUER, W.
               SAMANEN, JAMES
        (B) TITLE:   IDENTIFICATION OF A THIOETHER
             BY-PRODUCT
             IN THE SYNTHESIS OF A CYCLIC DISULFIDE PEPTIDE
             BY
             TANDEM MASS SPECTROMETRY
        (C) JOURNAL:   PROCEEDINGS OF THE 11TH AMERICAN
             PEPTIDE
             SYMPOSIUM
        (D) VOLUME:   ESCOM (LEIDEN 1990)
        (E) ISSUE:
        (F) PAGES:   443 - 445
        (G) DATE:   1990
        (H) DOCUMENT NUMBER:
        (I) FILING DATE:
        (J) PUBLICATION DATE:
        (K) RELEVANT RESIDUES IN SEQ ID NO: 12:   CYS-SER
             LANTHIONINE BRIDGE AND GENERAL PEPTIDE
             STRUCTURE (xiii) SEQUENCE DESCRIPTION:   SEQ ID NO: 12:

Cys Tyr Phe Gly Asn Ser Pro Arg Gly
```

```
1               5
```

(2) INFORMATION FOR SEQ ID NO: 13:

(i) SEQUENCE CHARACTERISTICS:
      (A) LENGTH:  9
      (B) TYPE:  AMINO ACID
      (C) TOPOLOGY:  LINEAR (ii) MOLECULE TYPE:
      (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
        COMMERCIALLY AVAILABLE FROM BECHAN BIOSCIENCE,
        INC.,
        3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
      (A) NAME/KEY:  N/A
      (B) LOCATION:  N/A
      (C) IDENTIFICATION METHOD:  N/A
      (D) OTHER INFORMATION:  water is removed and
         thereby
         a -S- bridge is present between Cys and Ser (x) PUBLICATION INFORMATION:
      (A) AUTHORS:  JUNG, GUNTHER
      (B) TITLE:  PEPTIDES WITH SULFIDE BRIDGES AND
         DEHYDROAMINO ACIDS:  THEIR PREPROPEPTIDES AND
         POSSIBILITIES FOR BIOENGINEERING
      (C) JOURNAL:  PROCEEDINGS OF THE 11TH AMERICAN
         PEPTIDE
         SYMPOSIUM
      (D) VOLUME:  ESCOM (LEIDEN 1990)
      (E) ISSUE:
      (F) PAGES:  865 - 869
      (G) DATE:  1990
      (H) DOCUMENT NUMBER:
      (I) FILING DATE:
      (J) PUBLICATION DATE:
      (K) RELEVANT RESIDUES IN SEQ ID NO: 13:  CYS-SER
         LANTHIONINE BRIDGE (xi) PUBLICATION INFORMATION:
      (A) AUTHORS:  SHIBA, TETSUO
         WAKAMIYA, TATEAKI
         FUKASE, KOICHI
         SANO, AKIHIKO
         SHIMBO, KUNIAKI
         UEKI, YASMYUKI
      (B) TITLE:  CHEMISTRY OF LANTHIONINE PEPTIDES
      (C) JOURNAL:  BIOPOLYMERS
      (D) VOLUME:  JOHN WILEY AND SONS, INC.
      (E) ISSUE:  SUPPLEMENTARY
      (F) PAGES:  511 - 519
      (G) DATE:  1986
      (H) DOCUMENT NUMBER:
      (I) FILING DATE:
      (J) PUBLICATION DATE:
      (K) RELEVANT RESIDUES IN SEQ ID NO: 13:  CYS-SER
         LANTHIONINE BRIDGE (xii) PUBLICATION INFORMATION:
      (A) AUTHORS:  BEAN, MARK F.
         CARR, STEVEN A.
         ESCHER, EMANUEL
         NEUGEBAUER, W.
         SAMANEN, JAMES (B) TITLE:  IDENTIFICATION OF A THIOETHER
            BY-PRODUCT
            IN THE SYNTHESIS OF A CYCLIC DISULFIDE PEPTIDE
            BY
            TANDEM MASS SPECTROMETRY
        (C) JOURNAL:  PROCEEDINGS OF THE 11TH AMERICAN
            PEPTIDE
            SYMPOSIUM
        (D) VOLUME:  ESCOM (LEIDEN 1990)
        (E) ISSUE:
        (F) PAGES:  443 - 445
        (G) DATE:  1990
        (H) DOCUMENT NUMBER:
        (I) FILING DATE:
        (J) PUBLICATION DATE:
        (K) RELEVANT RESIDUES IN SEQ ID NO: 13:  CYS-SER
            LANTHIONINE BRIDGE (xiii) SEQUENCE DESCRIPTION:  SEQ ID NO: 13:

Cys Tyr Ile Gly Asn Ser Pro Arg Gly
1               5

(2) INFORMATION FOR SEQ ID NO: 14:

(i) SEQUENCE CHARACTERISTICS:
         (A) LENGTH:  9
         (B) TYPE:  AMINO ACID
         (C) TOPOLOGY:  LINEAR (ii) MOLECULE TYPE:
         (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
             COMMERCIALLY AVAILABLE FROM BECHAN BIOSCIENCE,
             INC.,
             3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
         (A) NAME/KEY:  N/A
         (B) LOCATION:  N/A
         (C) IDENTIFICATION METHOD:  N/A
         (D) OTHER INFORMATION:  water is removed and
             thereby
             a -S- bridge is present between Cys and Ser (x) PUBLICATION INFORMATION:
         (A) AUTHORS:  JUNG, GUNTHER
         (B) TITLE:  PEPTIDES WITH SULFIDE BRIDGES AND
             DEHYDROAMINO ACIDS:  THEIR PREPROPEPTIDES AND
             POSSIBILITIES FOR BIOENGINEERING
         (C) JOURNAL:  PROCEEDINGS OF THE 11TH AMERICAN
             PEPTIDE
             SYMPOSIUM
         (D) VOLUME:  ESCOM (LEIDEN 1990)
         (E) ISSUE:
         (F) PAGES:  865 - 869
         (G) DATE:  1990
         (H) DOCUMENT NUMBER:
         (I) FILING DATE:
         (J) PUBLICATION DATE:
         (K) RELEVANT RESIDUES IN SEQ ID NO: 14:  CYS-SER
             LANTHIONINE BRIDGE (xi) PUBLICATION INFORMATION:
         (A) AUTHORS:  SHIBA, TETSUO
             WAKAMIYA, TATEAKI
             FUKASE, KOICHI

```
                        SANO, AKIHIKO
                        SHIMBO, KUNIAKI
                        UEKI, YASMYUKI
              (B) TITLE:  CHEMISTRY OF LANTHIONINE PEPTIDES
              (C) JOURNAL:  BIOPOLYMERS
              (D) VOLUME:  JOHN WILEY AND SONS, INC.
              (E) ISSUE:  SUPPLEMENTARY
              (F) PAGES:  511 - 519
              (G) DATE:  1986
              (H) DOCUMENT NUMBER:
              (I) FILING DATE:
              (J) PUBLICATION DATE:
              (K) RELEVANT RESIDUES IN SEQ ID NO: 14:  CYS-SER
                  LANTHIONINE BRIDGE (xii) PUBLICATION INFORMATION:
              (A) AUTHORS:  BEAN, MARK F.
                        CARR, STEVEN A.
                        ESCHER, EMANUEL
                        NEUGEBAUER, W.
                        SAMANEN, JAMES
              (B) TITLE:  IDENTIFICATION OF A THIOETHER
                        BY-PRODUCT
                        IN THE SYNTHESIS OF A CYCLIC DISULFIDE PEPTIDE
                        BY
                        TANDEM MASS SPECTROMETRY
              (C) JOURNAL:  PROCEEDINGS OF THE 11TH AMERICAN
                        PEPTIDE
                        SYMPOSIUM
              (D) VOLUME:  ESCOM (LEIDEN 1990)
              (E) ISSUE:
              (F) PAGES:  443 - 445
              (G) DATE:  1990
              (H) DOCUMENT NUMBER:
              (I) FILING DATE:
              (J) PUBLICATION DATE:
              (K) RELEVANT RESIDUES IN SEQ ID NO: 14:  CYS-SER
                  LANTHIONINE BRIDGE (xiii) SEQUENCE DESCRIPTION:  SEQ ID NO: 14:

Cys Tyr Phe Gly Asn Ser Pro Leu Gly
1               5

(2) INFORMATION FOR SEQ ID NO: 15:

(i) SEQUENCE CHARACTERISTICS:
              (A) LENGTH:  9
              (B) TYPE:  AMINO ACID
              (C) TOPOLOGY:  LINEAR (ii) MOLECULE TYPE:
              (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
                  COMMERCIALLY AVAILABLE FROM BECHAN BIOSCIENCE,
                  INC.,
                  3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
              (A) NAME/KEY:  N/A
              (B) LOCATION:  N/A
              (C) IDENTIFICATION METHOD:  N/A
              (D) OTHER INFORMATION:  water is removed and
                        thereby
                        a -S- bridge is present between Cys and Ser (x) PUBLICATION INFORMATION:
```

```
            (A) AUTHORS: JUNG, GUNTHER
            (B) TITLE: PEPTIDES WITH SULFIDE BRIDGES AND
                DEHYDROAMINO ACIDS: THEIR PREPROPEPTIDES AND
                POSSIBILITIES FOR BIOENGINEERING
            (C) JOURNAL: PROCEEDINGS OF THE 11TH AMERICAN
                PEPTIDE
                SYMPOSIUM
            (D) VOLUME: ESCOM (LEIDEN 1990)
            (E) ISSUE:
            (F) PAGES: 865 - 869
            (G) DATE: 1990
            (H) DOCUMENT NUMBER:
            (I) FILING DATE:
            (J) PUBLICATION DATE:
            (K) RELEVANT RESIDUES IN SEQ ID NO: 15: CYS-SER
                LANTHIONINE BRIDGE (xi) PUBLICATION INFORMATION:
            (A) AUTHORS: SHIBA, TETSUO
                WAKAMIYA, TATEAKI
                FUKASE, KOICHI
                SANO, AKIHIKO
                SHIMBO, KUNIAKI
                UEKI, YASMYUKI
            (B) TITLE: CHEMISTRY OF LANTHIONINE PEPTIDES
            (C) JOURNAL: BIOPOLYMERS
            (D) VOLUME: JOHN WILEY AND SONS, INC.
            (E) ISSUE: SUPPLEMENTARY
            (F) PAGES: 511 - 519
            (G) DATE: 1986
            (H) DOCUMENT NUMBER:
            (I) FILING DATE:
            (J) PUBLICATION DATE:
            (K) RELEVANT RESIDUES IN SEQ ID NO: 15: CYS-SER
                LANTHIONINE BRIDGE (xii) PUBLICATION INFORMATION:
            (A) AUTHORS: BEAN, MARK F.
                CARR, STEVEN A.
                ESCHER, EMANUEL
                NEUGEBAUER, W.
                SAMANEN, JAMES
            (B) TITLE: IDENTIFICATION OF A THIOETHER
                BY-PRODUCT
                IN THE SYNTHESIS OF A CYCLIC DISULFIDE PEPTIDE
                BY
                TANDEM MASS SPECTROMETRY
            (C) JOURNAL: PROCEEDINGS OF THE 11TH AMERICAN
                PEPTIDE
                SYMPOSIUM
            (D) VOLUME: ESCOM (LEIDEN 1990)
            (E) ISSUE:
            (F) PAGES: 443 - 445
            (G) DATE: 1990
            (H) DOCUMENT NUMBER:
            (I) FILING DATE:
            (J) PUBLICATION DATE:
            (K) RELEVANT RESIDUES IN SEQ ID NO: 15: CYS-SER
                LANTHIONINE BRIDGE (xiii) SEQUENCE DESCRIPTION: SEQ ID NO: 15:

Cys Tyr Ile Gly Asn Ser Pro Leu Gly
1               5

(2) INFORMATION FOR SEQ ID NO: 16:

(i) SEQUENCE CHARACTERISTICS:
            (A) LENGTH: 32
            (B) TYPE: AMINO ACID
            (C) TOPOLOGY: LINEAR (ii) MOLECULE TYPE:
            (A) DESCRIPTION: PEPTIDE (iii) HYPOTHETICAL: N/A (iv) ANTI-SENSE: N/A
```

```
     (v) FRAGMENT TYPE:  INTERNAL (vi) ORIGINAL SOURCE:  AMINO ACIDS LISTED IN SEQUENCE -
             COMMERCIALLY AVAILABLE FROM BECHAN BIOSCIENCE,
             INC.,
             3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
        (A) NAME/KEY:  N/A
        (B) LOCATION:  N/A
        (C) IDENTIFICATION METHOD:  N/A
        (D) OTHER INFORMATION:  water is removed and
            thereby
            a -S- bridge is present between Cys and the
            second Ser (x) PUBLICATION INFORMATION:
        (A) AUTHORS:  JUNG, GUNTHER
        (B) TITLE:  PEPTIDES WITH SULFIDE BRIDGES AND
            DEHYDROAMINO ACIDS:  THEIR PREPROPEPTIDES AND
            POSSIBILITIES FOR BIOENGINEERING
        (C) JOURNAL:  PROCEEDINGS OF THE 11TH AMERICAN
            PEPTIDE
            SYMPOSIUM
        (D) VOLUME:  ESCOM (LEIDEN 1990)
        (E) ISSUE:
        (F) PAGES:  865 - 869
        (G) DATE:  1990
        (H) DOCUMENT NUMBER:
        (I) FILING DATE:
        (J) PUBLICATION DATE:
        (K) RELEVANT RESIDUES IN SEQ ID NO: 16:  CYS-SER
            LANTHIONINE BRIDGE (xi) PUBLICATION INFORMATION:
        (A) AUTHORS:  SHIBA, TETSUO
            WAKAMIYA, TATEAKI
            FUKASE, KOICHI
            SANO, AKIHIKO
            SHIMBO, KUNIAKI
            UEKI, YASMYUKI
        (B) TITLE:  CHEMISTRY OF LANTHIONINE PEPTIDES
        (C) JOURNAL:  BIOPOLYMERS
        (D) VOLUME:  JOHN WILEY AND SONS, INC.
        (E) ISSUE:  SUPPLEMENTARY
        (F) PAGES:  511 - 519
        (G) DATE:  1986
        (H) DOCUMENT NUMBER:
        (I) FILING DATE:
        (J) PUBLICATION DATE:
        (K) RELEVANT RESIDUES IN SEQ ID NO: 16:  CYS-SER
            LANTHIONINE BRIDGE (xii) PUBLICATION INFORMATION:
        (A) AUTHORS:  BEAN, MARK F.
            CARR, STEVEN A.
            ESCHER, EMANUEL
            NEUGEBAUER, W.
            SAMANEN, JAMES
        (B) TITLE:  IDENTIFICATION OF A THIOETHER
            BY-PRODUCT
            IN THE SYNTHESIS OF A CYCLIC DISULFIDE PEPTIDE
            BY
            TANDEM MASS SPECTROMETRY
        (C) JOURNAL:  PROCEEDINGS OF THE 11TH AMERICAN
            PEPTIDE
            SYMPOSIUM
        (D) VOLUME:  ESCOM (LEIDEN 1990)
        (E) ISSUE:
        (F) PAGES:  443 - 445
        (G) DATE:  1990
        (H) DOCUMENT NUMBER:
        (I) FILING DATE:
        (J) PUBLICATION DATE:
```

```
            (K) RELEVANT RESIDUES IN SEQ ID NO: 16:  CYS-SER
                LANTHIONINE BRIDGE (xiii) SEQUENCE DESCRIPTION:  SEQ ID NO: 16:

Cys Gly Asn Leu Ser Thr Ser Val Leu Gly Lys Leu Ser Gln
1               5                   10

Glu Leu His Lys Leu Gln Thr Tyr Pro Arg Thr Asp Val Gly
15                  20                  25

Ala Gly Thr Pro
    30

(2) INFORMATION FOR SEQ ID NO: 17:

(i) SEQUENCE CHARACTERISTICS:
         (A) LENGTH:  32
         (B) TYPE:  AMINO ACID
         (C) TOPOLOGY:  LINEAR (ii) MOLECULE TYPE:
         (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
             COMMERCIALLY AVAILABLE FROM BECHAN BIOSCIENCE,
             INC.,
             3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
         (A) NAME/KEY:  N/A
         (B) LOCATION:  N/A
         (C) IDENTIFICATION METHOD:  N/A
         (D) OTHER INFORMATION:  water is removed and
             thereby a
             -S- bridge is present between Cys and the
             third Ser (x) PUBLICATION INFORMATION:
         (A) AUTHORS:  JUNG, GUNTHER
         (B) TITLE:  PEPTIDES WITH SULFIDE BRIDGES AND
             DEHYDROAMINO ACIDS:  THEIR PREPROPEPTIDES AND
             POSSIBILITIES FOR BIOENGINEERING
         (C) JOURNAL:  PROCEEDINGS OF THE 11TH AMERICAN
             PEPTIDE
             SYMPOSIUM
         (D) VOLUME:  ESCOM (LEIDEN 1990)
         (E) ISSUE:
         (F) PAGES:  865 - 869
         (G) DATE:  1990
         (H) DOCUMENT NUMBER:
         (I) FILING DATE:
         (J) PUBLICATION DATE:
         (K) RELEVANT RESIDUES IN SEQ ID NO: 17:  CYS-SER
             LANTHIONINE BRIDGE (xi) PUBLICATION INFORMATION:
         (A) AUTHORS:  SHIBA, TETSUO
             WAKAMIYA, TATEAKI
             FUKASE, KOICHI
             SANO, AKIHIKO
             SHIMBO, KUNIAKI
             UEKI, YASMYUKI
         (B) TITLE:  CHEMISTRY OF LANTHIONINE PEPTIDES
         (C) JOURNAL:  BIOPOLYMERS
         (D) VOLUME:  JOHN WILEY AND SONS, INC.
         (E) ISSUE:  SUPPLEMENTARY
         (F) PAGES:  511 - 519
```

```
              (G) DATE:  1986
              (H) DOCUMENT NUMBER:
              (I) FILING DATE:
              (J) PUBLICATION DATE:
              (K) RELEVANT RESIDUES IN SEQ ID NO: 17:  CYS-SER
                  LANTHIONINE BRIDGE (xii) PUBLICATION INFORMATION:
              (A) AUTHORS:  BEAN, MARK F.
                   CARR, STEVEN A.
                   ESCHER, EMANUEL
                   NEUGEBAUER, W.
                   SAMANEN, JAMES
              (B) TITLE:   IDENTIFICATION OF A THIOETHER
                  BY-PRODUCT
                  IN THE SYNTHESIS OF A CYCLIC DISULFIDE PEPTIDE
                  BY
                  TANDEM MASS SPECTROMETRY
              (C) JOURNAL:  PROCEEDINGS OF THE 11TH AMERICAN
                  PEPTIDE
                  SYMPOSIUM
              (D) VOLUME:  ESCOM (LEIDEN 1990)
              (E) ISSUE:
              (F) PAGES:   443 - 445
              (G) DATE:  1990
              (H) DOCUMENT NUMBER:
              (I) FILING DATE:
              (J) PUBLICATION DATE:
              (K) RELEVANT RESIDUES IN SEQ ID NO: 17:  CYS-SER
                  LANTHIONINE BRIDGE (xiii) SEQUENCE DESCRIPTION:  SEQ ID NO: 17:

Cys Ser Asn Leu Ser Thr Ser Val Leu Gly Lys Leu Ser Gln
1               5                   10

Glu Leu His Lys Leu Gln Thr Tyr Pro Arg Thr Asp Val Gly
15              20                  25

Ala Gly Thr Pro
    30

(2) INFORMATION FOR SEQ ID NO: 18:

(i) SEQUENCE CHARACTERISTICS:
              (A) LENGTH:  32
              (B) TYPE:  AMINO ACID
              (C) TOPOLOGY:  LINEAR (ii) MOLECULE TYPE:
              (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
                  COMMERCIALLY AVAILABLE FROM BECHAN BIOSCIENCE,
                  INC.,
                  3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
              (A) NAME/KEY:  N/A
              (B) LOCATION:  N/A
              (C) IDENTIFICATION METHOD:  N/A
              (D) OTHER INFORMATION:  water is removed and
                  thereby a
                  -S- bridge is present between Cys and the
                  second Ser (x) PUBLICATION INFORMATION:
              (A) AUTHORS:  JUNG, GUNTHER
```

(B) TITLE: PEPTIDES WITH SULFIDE BRIDGES AND
            DEHYDROAMINO ACIDS: THEIR PREPROPEPTIDES AND
            POSSIBILITIES FOR BIOENGINEERING
        (C) JOURNAL: PROCEEDINGS OF THE 11TH AMERICAN
            PEPTIDE
            SYMPOSIUM
        (D) VOLUME: ESCOM (LEIDEN 1990)
        (E) ISSUE:
        (F) PAGES: 865 - 869
        (G) DATE: 1990
        (H) DOCUMENT NUMBER:
        (I) FILING DATE:
        (J) PUBLICATION DATE:
        (K) RELEVANT RESIDUES IN SEQ ID NO: 18: CYS-SER
            LANTHIONINE BRIDGE (xi) PUBLICATION INFORMATION:
        (A) AUTHORS: SHIBA, TETSUO
            WAKAMIYA, TATEAKI
            FUKASE, KOICHI
            SANO, AKIHIKO
            SHIMBO, KUNIAKI
            UEKI, YASMYUKI
        (B) TITLE: CHEMISTRY OF LANTHIONINE PEPTIDES
        (C) JOURNAL: BIOPOLYMERS
        (D) VOLUME: JOHN WILEY AND SONS, INC.
        (E) ISSUE: SUPPLEMENTARY
        (F) PAGES: 511 - 519
        (G) DATE: 1986
        (H) DOCUMENT NUMBER:
        (I) FILING DATE:
        (J) PUBLICATION DATE:
        (K) RELEVANT RESIDUES IN SEQ ID NO: 18: CYS-SER
            LANTHIONINE BRIDGE (xii) PUBLICATION INFORMATION:
        (A) AUTHORS: BEAN, MARK F.
            CARR, STEVEN A.
            ESCHER, EMANUEL
            NEUGEBAUER, W.
            SAMANEN, JAMES
        (B) TITLE: IDENTIFICATION OF A THIOETHER
            BY-PRODUCT
            IN THE SYNTHESIS OF A CYCLIC DISULFIDE PEPTIDE
            BY
            TANDEM MASS SPECTROMETRY
        (C) JOURNAL: PROCEEDINGS OF THE 11TH AMERICAN
            PEPTIDE
            SYMPOSIUM
        (D) VOLUME: ESCOM (LEIDEN 1990)
        (E) ISSUE:
        (F) PAGES: 443 - 445
        (G) DATE: 1990
        (H) DOCUMENT NUMBER:
        (I) FILING DATE:
        (J) PUBLICATION DATE:
        (K) RELEVANT RESIDUES IN SEQ ID NO: 18: CYS-SER
            LANTHIONINE BRIDGE (xiii) SEQUENCE DESCRIPTION: SEQ ID NO: 18:

Cys Gly Asn Leu Ser Thr Ser Met Leu Gly Thr Tyr Thr Gln
1               5                   10

Asp Phe Asn Lys Phe His Thr Phe Pro Gln Thr Ala Ile Gly
15                  20                  25

Val Gly Ala Pro
    30

(2) INFORMATION FOR SEQ ID NO: 19:

(i) SEQUENCE CHARACTERISTICS:
        (A) LENGTH: 32
        (B) TYPE: AMINO ACID
        (C) TOPOLOGY: LINEAR (ii) MOLECULE TYPE:

(A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
             COMMERCIALLY AVAILABLE FROM BECHAN BIOSCIENCE,
             INC.,
             3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
        (A) NAME/KEY:  N/A
        (B) LOCATION:  N/A
        (C) IDENTIFICATION METHOD:  N/A
        (D) OTHER INFORMATION:  water is removed and
            thereby a
            -S- bridge is present between Cys and the
            third Ser (x) PUBLICATION INFORMATION:
        (A) AUTHORS:  JUNG, GUNTHER
        (B) TITLE:  PEPTIDES WITH SULFIDE BRIDGES AND
            DEHYDROAMINO ACIDS:  THEIR PREPROPEPTIDES AND
            POSSIBILITIES FOR BIOENGINEERING
        (C) JOURNAL:  PROCEEDINGS OF THE 11TH AMERICAN
            PEPTIDE
            SYMPOSIUM
        (D) VOLUME:  ESCOM (LEIDEN 1990)
        (E) ISSUE:
        (F) PAGES:  865 - 869
        (G) DATE:  1990
        (H) DOCUMENT NUMBER:
        (I) FILING DATE:
        (J) PUBLICATION DATE:
        (K) RELEVANT RESIDUES IN SEQ ID NO: 19:  CYS-SER
            LANTHIONINE BRIDGE (xi) PUBLICATION INFORMATION:
        (A) AUTHORS:  SHIBA, TETSUO
            WAKAMIYA, TATEAKI
            FUKASE, KOICHI
            SANO, AKIHIKO
            SHIMBO, KUNIAKI
            UEKI, YASMYUKI
        (B) TITLE:  CHEMISTRY OF LANTHIONINE PEPTIDES
        (C) JOURNAL:  BIOPOLYMERS
        (D) VOLUME:  JOHN WILEY AND SONS, INC.
        (E) ISSUE:  SUPPLEMENTARY
        (F) PAGES:  511 - 519
        (G) DATE:  1986
        (H) DOCUMENT NUMBER:
        (I) FILING DATE:
        (J) PUBLICATION DATE:
        (K) RELEVANT RESIDUES IN SEQ ID NO: 19:  CYS-SER
            LANTHIONINE BRIDGE (xii) PUBLICATION INFORMATION:
        (A) AUTHORS:  BEAN, MARK F.
            CARR, STEVEN A.
            ESCHER, EMANUEL
            NEUGEBAUER, W.
            SAMANEN, JAMES
        (B) TITLE:  IDENTIFICATION OF A THIOETHER
            BY-PRODUCT
            IN THE SYNTHESIS OF A CYCLIC DISULFIDE PEPTIDE
            BY
            TANDEM MASS SPECTROMETRY
        (C) JOURNAL:  PROCEEDINGS OF THE 11TH AMERICAN
            PEPTIDE
            SYMPOSIUM
        (D) VOLUME:  ESCOM (LEIDEN 1990)
        (E) ISSUE:

-continued

```
            (F) PAGES: 443 - 445
            (G) DATE: 1990
            (H) DOCUMENT NUMBER:
            (I) FILING DATE:
            (J) PUBLICATION DATE:
            (K) RELEVANT RESIDUES IN SEQ ID NO: 19:  CYS-SER
                LANTHIONINE BRIDGE (xiii) SEQUENCE DESCRIPTION: SEQ ID NO: 19:

Cys Ser Asn Leu Ser Thr Ser Met Leu Gly Thr Tyr Thr Gln
1               5                   10

Asp Phe Asn Lys Phe His Thr Phe Pro Gln Thr Ala Ile Gly
15                  20                  25

Val Gly Ala Pro
        30

(2) INFORMATION FOR SEQ ID NO: 20:

(i) SEQUENCE CHARACTERISTICS:
           (A) LENGTH:  32
           (B) TYPE:  AMINO ACID
           (C) TOPOLOGY:  LINEAR (ii) MOLECULE TYPE:
           (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
                COMMERCIALLY AVAILABLE FROM BECHAN BIOSCIENCE,
                INC.,
                3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
           (A) NAME/KEY:  N/A
           (B) LOCATION:  N/A
           (C) IDENTIFICATION METHOD:  N/A
           (D) OTHER INFORMATION:  water is removed and
               thereby a
               -S- bridge is present between Cys and the
               third Ser (x) PUBLICATION INFORMATION:
           (A) AUTHORS:  JUNG, GUNTHER
           (B) TITLE:  PEPTIDES WITH SULFIDE BRIDGES AND
               DEHYDROAMINO ACIDS:  THEIR PREPROPEPTIDES AND
               POSSIBILITIES FOR BIOENGINEERING
           (C) JOURNAL:  PROCEEDINGS OF THE 11TH AMERICAN
               PEPTIDE
               SYMPOSIUM
           (D) VOLUME:  ESCOM (LEIDEN 1990)
           (E) ISSUE:
           (F) PAGES: 865 - 869
           (G) DATE: 1990
           (H) DOCUMENT NUMBER:
           (I) FILING DATE:
           (J) PUBLICATION DATE:
           (K) RELEVANT RESIDUES IN SEQ ID NO: 20:  CYS-SER
               LANTHIONINE BRIDGE (xi) PUBLICATION INFORMATION:
           (A) AUTHORS:  SHIBA, TETSUO
                         WAKAMIYA, TATEAKI
                         FUKASE, KOICHI
                         SANO, AKIHIKO
                         SHIMBO, KUNIAKI
                         UEKI, YASMYUKI
```

```
            (B) TITLE:  CHEMISTRY OF LANTHIONINE PEPTIDES
            (C) JOURNAL:  BIOPOLYMERS
            (D) VOLUME:  JOHN WILEY AND SONS, INC.
            (E) ISSUE:  SUPPLEMENTARY
            (F) PAGES:  511 - 519
            (G) DATE:  1986
            (H) DOCUMENT NUMBER:
            (I) FILING DATE:
            (J) PUBLICATION DATE:
            (K) RELEVANT RESIDUES IN SEQ ID NO: 20:  CYS-SER
                LANTHIONINE BRIDGE (xii) PUBLICATION INFORMATION:
            (A) AUTHORS:  BEAN, MARK F.
                CARR, STEVEN A.
                ESCHER, EMANUEL
                NEUGEBAUER, W.
                SAMANEN, JAMES
            (B) TITLE:  IDENTIFICATION OF A THIOETHER
                BY-PRODUCT
                IN THE SYNTHESIS OF A CYCLIC DISULFIDE PEPTIDE
                BY
                TANDEM MASS SPECTROMETRY
            (C) JOURNAL:  PROCEEDINGS OF THE 11TH AMERICAN
                PEPTIDE
                SYMPOSIUM
            (D) VOLUME:  ESCOM (LEIDEN 1990)
            (E) ISSUE:
            (F) PAGES:  443 - 445
            (G) DATE:  1990
            (H) DOCUMENT NUMBER:
            (I) FILING DATE:
            (J) PUBLICATION DATE:
            (K) RELEVANT RESIDUES IN SEQ ID NO: 20:  CYS-SER
                LANTHIONINE BRIDGE (xiii) SEQUENCE DESCRIPTION:  SEQ ID NO: 20:

Cys Ser Asn Leu Ser Thr Ser Val Leu Gly Lys Leu Ser Gln
1               5                   10

Glu Leu His Lys Leu Gln Thr Tyr Pro Arg Thr Asn Thr Gly
15              20                  25

Ser Gly Thr Pro
    30

(2) INFORMATION FOR SEQ ID NO: 21:

(i) SEQUENCE CHARACTERISTICS:
        (A) LENGTH:  32
        (B) TYPE:  AMINO ACID
        (C) TOPOLOGY:  LINEAR (ii) MOLECULE TYPE:
        (A) DESCRIPTION:  PEPTIDE (iii) HYPOTHETICAL:  N/A (iv) ANTI-SENSE:  N/A (v) FRAGMENT TYPE:  INTERNAL (vi) ORIGINAL SOURCE:  AMINO ACIDS LISTED IN SEQUENCE -
            COMMERCIALLY AVAILABLE FROM BECHAN BIOSCIENCE,
            INC.,
            3700 MARKET STREET, PHILADELPHIA, PA  19104

(vii) IMMEDIATE SOURCE:  SYNTHESIZED PEPTIDE (viii) POSITION IN GENOME:  N/A (ix) FEATURE:
        (A) NAME/KEY:  N/A
        (B) LOCATION:  N/A
        (C) IDENTIFICATION METHOD:  N/A
        (D) OTHER INFORMATION:  water is removed and
            thereby a
```

```
            -S- bridge is present between Cys and the
            second Ser (x) PUBLICATION INFORMATION:
        (A) AUTHORS:  JUNG, GUNTHER
        (B) TITLE:  PEPTIDES WITH SULFIDE BRIDGES AND
            DEHYDROAMINO ACIDS:  THEIR PREPROPEPTIDES AND
            POSSIBILITIES FOR BIOENGINEERING
        (C) JOURNAL:  PROCEEDINGS OF THE 11TH AMERICAN
            PEPTIDE
            SYMPOSIUM
        (D) VOLUME:  ESCOM (LEIDEN 1990)
        (E) ISSUE:
        (F) PAGES:  865 - 869
        (G) DATE:  1990
        (H) DOCUMENT NUMBER:
        (I) FILING DATE:
        (J) PUBLICATION DATE:
        (K) RELEVANT RESIDUES IN SEQ ID NO: 21:  CYS-SER
            LANTHIONINE BRIDGE (xi) PUBLICATION INFORMATION:
        (A) AUTHORS:  SHIBA, TETSUO
            WAKAMIYA, TATEAKI
            FUKASE, KOICHI
            SANO, AKIHIKO
            SHIMBO, KUNIAKI
            UEKI, YASMYUKI
        (B) TITLE:  CHEMISTRY OF LANTHIONINE PEPTIDES
        (C) JOURNAL:  BIOPOLYMERS
        (D) VOLUME:  JOHN WILEY AND SONS, INC.
        (E) ISSUE:  SUPPLEMENTARY
        (F) PAGES:  511 - 519
        (G) DATE:  1986
        (H) DOCUMENT NUMBER:
        (I) FILING DATE:
        (J) PUBLICATION DATE:
        (K) RELEVANT RESIDUES IN SEQ ID NO: 21:  CYS-SER
            LANTHIONINE BRIDGE (xii) PUBLICATION INFORMATION:
        (A) AUTHORS:  BEAN, MARK F.
            CARR, STEVEN A.
            ESCHER, EMANUEL
            NEUGEBAUER, W.
            SAMANEN, JAMES
        (B) TITLE:  IDENTIFICATION OF A THIOETHER
            BY-PRODUCT
            IN THE SYNTHESIS OF A CYCLIC DISULFIDE PEPTIDE
            BY
            TANDEM MASS SPECTROMETRY
        (C) JOURNAL:  PROCEEDINGS OF THE 11TH AMERICAN
            PEPTIDE
            SYMPOSIUM
        (D) VOLUME:  ESCOM (LEIDEN 1990)
        (E) ISSUE:
        (F) PAGES:  443 - 445
        (G) DATE:  1990
        (H) DOCUMENT NUMBER:
        (I) FILING DATE:
        (J) PUBLICATION DATE:
        (K) RELEVANT RESIDUES IN SEQ ID NO: 21:  CYS-SER
            LANTHIONINE BRIDGE (xiii) SEQUENCE DESCRIPTION:  SEQ ID NO: 21:

Cys Gly Asn Leu Ser Thr Ser Val Leu Gly Lys Leu Ser Gln
1               5                   10

Glu Leu His Lys Leu Gln Thr Tyr Pro Arg Thr Asn Thr Gly
15                  20                  25

Ser Gly Thr Pro
    30

(2) INFORMATION FOR SEQ ID NO: 22:

(i) SEQUENCE CHARACTERISTICS:
```

```
           (A) LENGTH: 21
           (B) TYPE: AMINO ACID
           (C) TOPOLOGY: LINEAR (ii) MOLECULE TYPE:
           (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: AMINO ACIDS LISTED IN SEQUENCE -
           COMMERCIALLY AVAILABLE FROM BECHAN BIOSCIENCE,
           INC.,
           3700 MARKET STREET, PHILADELPHIA, PA  19104

(vii) IMMEDIATE SOURCE: SYNTHESIZED PEPTIDE (viii) POSITION IN GENOME: N/A (ix) FEATURE: N/A
           (A) NAME/KEY: N/A
           (B) LOCATION: N/A
           (C) IDENTIFICATION METHOD: N/A
           (D) OTHER INFORMATION: water is removed and
               thereby a
               -S- bridge is present between Cys and the
               fourth Ser
               and a -S-S- bridge thereby is present between
               the
               second and third Cys (x) PUBLICATION INFORMATION:
           (A) AUTHORS: JUNG, GUNTHER
           (B) TITLE: PEPTIDES WITH SULFIDE BRIDGES AND
               DEHYDROAMINO ACIDS: THEIR PREPROPEPTIDES AND
               POSSIBILITIES FOR BIOENGINEERING
           (C) JOURNAL: PROCEEDINGS OF THE 11TH AMERICAN
               PEPTIDE
               SYMPOSIUM
           (D) VOLUME: ESCOM (LEIDEN 1990)
           (E) ISSUE:
           (F) PAGES: 865 - 869
           (G) DATE: 1990
           (H) DOCUMENT NUMBER:
           (I) FILING DATE:
           (J) PUBLICATION DATE:
           (K) RELEVANT RESIDUES IN SEQ ID NO: 22: CYS-SER
               LANTHIONINE BRIDGE (xi) PUBLICATION INFORMATION:
           (A) AUTHORS: SHIBA, TETSUO
               WAKAMIYA, TATEAKI
               FUKASE, KOICHI
               SANO, AKIHIKO
               SHIMBO, KUNIAKI
               UEKI, YASMYUKI
           (B) TITLE: CHEMISTRY OF LANTHIONINE PEPTIDES
           (C) JOURNAL: BIOPOLYMERS
           (D) VOLUME: JOHN WILEY AND SONS, INC.
           (E) ISSUE: SUPPLEMENTARY
           (F) PAGES: 511 - 519
           (G) DATE: 1986
           (H) DOCUMENT NUMBER:
           (I) FILING DATE:
           (J) PUBLICATION DATE:
           (K) RELEVANT RESIDUES IN SEQ ID NO: 22: CYS-SER
               LANTHIONINE BRIDGE (xii) PUBLICATION INFORMATION:
           (A) AUTHORS: BEAN, MARK F.
               CARR, STEVEN A.
               ESCHER, EMANUEL
               NEUGEBAUER, W.
               SAMANEN, JAMES
           (B) TITLE: IDENTIFICATION OF A THIOETHER
               BY-PRODUCT
```

```
                    IN THE SYNTHESIS OF A CYCLIC DISULFIDE PEPTIDE
                    BY
                    TANDEM MASS SPECTROMETRY
               (C) JOURNAL:  PROCEEDINGS OF THE 11TH AMERICAN
                    PEPTIDE
                    SYMPOSIUM
               (D) VOLUME:   ESCOM (LEIDEN 1990)
               (E) ISSUE:
               (F) PAGES:    443 - 445
               (G) DATE:     1990
               (H) DOCUMENT NUMBER:
               (I) FILING DATE:
               (J) PUBLICATION DATE:
               (K) RELEVANT RESIDUES IN SEQ ID NO: 22:  CYS-SER
                    LANTHIONINE BRIDGE (xiii) SEQUENCE DESCRIPTION:  SEQ ID NO: 22:

Cys Ser Cys Ser Ser Leu Met Asp Lys Glu Cys Val Tyr Phe
1               5                   10

Ser His Leu Asp Ile Ile Trp
15                  20

(2) INFORMATION FOR SEQ ID NO: 23:

(i) SEQUENCE CHARACTERISTICS:
          (A) LENGTH:  21
          (B) TYPE:  AMINO ACID
          (C) TOPOLOGY:  LINEAR (ii) MOLECULE TYPE:
          (A) DESCRIPTION:  PEPTIDE (iii) HYPOTHETICAL:  N/A (iv) ANTI-SENSE:  N/A (v) FRAGMENT TYPE:   INTERNAL (vi) ORIGINAL SOURCE:  AMINO ACIDS LISTED IN SEQUENCE -
              COMMERCIALLY AVAILABLE FROM BECHAN BIOSCIENCE,
              INC.,
              3700 MARKET STREET, PHILADELPHIA, PA  19104

(vii) IMMEDIATE SOURCE:   SYNTHESIZED PEPTIDE (viii) POSITION IN GENOME:  N/A (ix) FEATURE:
          (A) NAME/KEY:  N/A
          (B) LOCATION:  N/A
          (C) IDENTIFICATION METHOD:  N/A
          (D) OTHER INFORMATION:  water is removed and
              thereby a
              -S- bridge is present between the second Cys
              and the
              fourth Ser and a -S-S- bridge thereby is
              present
              between the first and third Cys (x) PUBLICATION INFORMATION:
          (A) AUTHORS:  JUNG, GUNTHER
          (B) TITLE:   PEPTIDES WITH SULFIDE BRIDGES AND
              DEHYDROAMINO ACIDS:  THEIR PREPROPEPTIDES AND
              POSSIBILITIES FOR BIOENGINEERING
          (C) JOURNAL:  PROCEEDINGS OF THE 11TH AMERICAN
              PEPTIDE
              SYMPOSIUM
          (D) VOLUME:   ESCOM (LEIDEN 1990)
          (E) ISSUE:
          (F) PAGES:    865 - 869
          (G) DATE:     1990
          (H) DOCUMENT NUMBER:
          (I) FILING DATE:
          (J) PUBLICATION DATE:
          (K) RELEVANT RESIDUES IN SEQ ID NO: 23:  CYS-SER
              LANTHIONINE BRIDGE
```

```
    (xi) PUBLICATION INFORMATION:
         (A) AUTHORS: SHIBA, TETSUO
                 WAKAMIYA, TATEAKI
                 FUKASE, KOICHI
                 SANO, AKIHIKO
                 SHIMBO, KUNIAKI
                 UEKI, YASMYUKI
         (B) TITLE:   CHEMISTRY OF LANTHIONINE PEPTIDES
         (C) JOURNAL: BIOPOLYMERS
         (D) VOLUME:  JOHN WILEY AND SONS, INC.
         (E) ISSUE:   SUPPLEMENTARY
         (F) PAGES:   511 - 519
         (G) DATE:    1986
         (H) DOCUMENT NUMBER:
         (I) FILING DATE:
         (J) PUBLICATION DATE:
         (K) RELEVANT RESIDUES IN SEQ ID NO: 23:  CYS-SER
                 LANTHIONINE BRIDGE (xii) PUBLICATION INFORMATION:
         (A) AUTHORS: BEAN, MARK F.
                 CARR, STEVEN A.
                 ESCHER, EMANUEL
                 NEUGEBAUER, W.
                 SAMANEN, JAMES
         (B) TITLE:   IDENTIFICATION OF A THIOETHER
                 BY-PRODUCT
                 IN THE SYNTHESIS OF A CYCLIC DISULFIDE PEPTIDE
                 BY
                 TANDEM MASS SPECTROMETRY
         (C) JOURNAL: PROCEEDINGS OF THE 11TH AMERICAN
                 PEPTIDE
                 SYMPOSIUM
         (D) VOLUME:  ESCOM (LEIDEN 1990)
         (E) ISSUE:
         (F) PAGES:   443 - 445
         (G) DATE:    1990
         (H) DOCUMENT NUMBER:
         (I) FILING DATE:
         (J) PUBLICATION DATE:
         (K) RELEVANT RESIDUES IN SEQ ID NO: 23:  CYS-SER
                 LANTHIONINE BRIDGE (xiii) SEQUENCE DESCRIPTION:  SEQ ID NO: 23:

Cys Ser Cys Ser Ser Leu Met Asp Lys Glu Ser Val Tyr Phe
1               5                   10

Cys His Leu Asp Ile Ile Trp
15                  20

(2) INFORMATION FOR SEQ ID NO: 24:

(i) SEQUENCE CHARACTERISTICS:
         (A) LENGTH: 21
         (B) TYPE:   AMINO ACID
         (C) TOPOLOGY: LINEAR (ii) MOLECULE TYPE:
         (A) DESCRIPTION: PEPTIDE (iii) HYPOTHETICAL: N/A (iv) ANTI-SENSE: N/A (v) FRAGMENT TYPE: INTERNAL (vi) ORIGINAL SOURCE: AMINO ACIDS LISTED IN SEQUENCE -
             COMMERCIALLY AVAILABLE FROM BECHAN BIOSCIENCE,
             INC.,
             3700 MARKET STREET, PHILADELPHIA, PA  19104

(vii) IMMEDIATE SOURCE: SYNTHESIZED PEPTIDE (viii) POSITION IN GENOME: N/A (ix) FEATURE:
```

```
            (A) NAME/KEY:  N/A
            (B) LOCATION:  N/A
            (C) IDENTIFICATION METHOD:  N/A
            (D) OTHER INFORMATION:  water is removed and
                  thereby a
                  -S- bridge is present between the first Cys
                  and the
                  fifth Ser and a -S- bridge thereby is present
                  between the second Cys and the fourth Cyr (x) PUBLICATION INFORMATION:
            (A) AUTHORS:  JUNG, GUNTHER
            (B) TITLE:  PEPTIDES WITH SULFIDE BRIDGES AND
                  DEHYDROAMINO ACIDS:  THEIR PREPROPEPTIDES AND
                  POSSIBILITIES FOR BIOENGINEERING
            (C) JOURNAL:  PROCEEDINGS OF THE 11TH AMERICAN
                  PEPTIDE
                  SYMPOSIUM
            (D) VOLUME:  ESCOM (LEIDEN 1990)
            (E) ISSUE:
            (F) PAGES:  865 - 869
            (G) DATE:  1990
            (H) DOCUMENT NUMBER:
            (I) FILING DATE:
            (J) PUBLICATION DATE:
            (K) RELEVANT RESIDUES IN SEQ ID NO: 24:  CYS-SER
                  LANTHIONINE BRIDGE (xi) PUBLICATION INFORMATION:
            (A) AUTHORS:  SHIBA, TETSUO
                  WAKAMIYA, TATEAKI
                  FUKASE, KOICHI
                  SANO, AKIHIKO
                  SHIMBO, KUNIAKI
                  UEKI, YASMYUKI
            (B) TITLE:  CHEMISTRY OF LANTHIONINE PEPTIDES
            (C) JOURNAL:  BIOPOLYMERS
            (D) VOLUME:  JOHN WILEY AND SONS, INC.
            (E) ISSUE:  SUPPLEMENTARY
            (F) PAGES:  511 - 519
            (G) DATE:  1986
            (H) DOCUMENT NUMBER:
            (I) FILING DATE:
            (J) PUBLICATION DATE:
            (K) RELEVANT RESIDUES IN SEQ ID NO: 24:  CYS-SER
                  LANTHIONINE BRIDGE (xii) PUBLICATION INFORMATION:
            (A) AUTHORS:  BEAN, MARK F.
                  CARR, STEVEN A.
                  ESCHER, EMANUEL
                  NEUGEBAUER, W.
                  SAMANEN, JAMES
            (B) TITLE:  IDENTIFICATION OF A THIOETHER
                  BY-PRODUCT
                  IN THE SYNTHESIS OF A CYCLIC DISULFIDE PEPTIDE
                  BY
                  TANDEM MASS SPECTROMETRY
            (C) JOURNAL:  PROCEEDINGS OF THE 11TH AMERICAN
                  PEPTIDE
                  SYMPOSIUM
            (D) VOLUME:  ESCOM (LEIDEN 1990)
            (E) ISSUE:
            (F) PAGES:  443 - 445
            (G) DATE:  1990
            (H) DOCUMENT NUMBER:
            (I) FILING DATE:
            (J) PUBLICATION DATE:
            (K) RELEVANT RESIDUES IN SEQ ID NO: 24:  CYS-SER
                  LANTHIONINE BRIDGE (xiii) SEQUENCE DESCRIPTION:  SEQ ID NO: 24:

Cys Ser Cys Ser Ser Leu Met Asp Lys Glu Ser Val Tyr Phe
1               5                   10

Ser His Leu Asp Ile Ile Trp
15                  20
```